US012721808B2

(12) United States Patent
Rozga et al.

(10) Patent No.: US 12,721,808 B2
(45) Date of Patent: Sep. 1, 2026

(54) ORRIS ROOT EXTRACTS, COMPOSITIONS, AND METHODS FOR SKIN APPLICATIONS

(71) Applicant: ACCESS BUSINESS GROUP INTERNATIONAL LLC, Ada, MI (US)

(72) Inventors: Lisa A. Rozga, Huntington Beach, CA (US); Mickeala Tu, Walnut, CA (US); Stephen R. Missler, Grand Rapids, MI (US); Sunghan Yim, Ada, MI (US); Timothy Mulder, Allendale, MI (US); Rhonda Solberg, Grand Rapids, MI (US); Alexandria Smith, Redondo Beach, CA (US); Sudhir Baswan, Grand Rapids, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 240 days.

(21) Appl. No.: 18/566,536

(22) PCT Filed: Jun. 2, 2022

(86) PCT No.: PCT/US2022/031882
§ 371 (c)(1),
(2) Date: Dec. 1, 2023

(87) PCT Pub. No.: WO2022/256476
PCT Pub. Date: Dec. 8, 2022

(65) Prior Publication Data

US 2024/0245600 A1 Jul. 25, 2024

Related U.S. Application Data

(60) Provisional application No. 63/197,132, filed on Jun. 4, 2021.

(51) Int. Cl.

| | |
|---|---|
| ***A61K 36/00*** | (2006.01) |
| ***A61K 8/33*** | (2006.01) |
| ***A61K 8/60*** | (2006.01) |
| ***A61K 8/9794*** | (2017.01) |
| ***A61Q 19/02*** | (2006.01) |
| ***A61Q 19/04*** | (2006.01) |

(52) U.S. Cl.
CPC .............. *A61K 8/9794* (2017.08); *A61K 8/33* (2013.01); *A61K 8/602* (2013.01); *A61Q 19/02* (2013.01); *A61Q 19/04* (2013.01)

(58) Field of Classification Search
CPC ...................................................... A61Q 19/02
See application file for complete search history.

(56) References Cited

U.S. PATENT DOCUMENTS

| | | | |
|---|---|---|---|
| 2015/0290097 A1 | 10/2015 | Nakamura et al. | |
| 2020/0147004 A1* | 5/2020 | Detmar | A61K 8/345 |

FOREIGN PATENT DOCUMENTS

| | | |
|---|---|---|
| CN | 112494402 A | 3/2021 |
| FR | 3055214 A1 | 3/2018 |
| JP | H0859536 A | 3/1996 |
| JP | H0930954 A | 2/1997 |
| JP | H09241154 A | 9/1997 |
| WO | 200234229 A1 | 5/2002 |
| WO | 2012175868 A2 | 12/2012 |

OTHER PUBLICATIONS

International Search Report for PCT/US2022/031882 dated Oct. 20, 2022, 6 pages.
Machine assisted English translation of CN112494402A obtained from https://worldwide.espacenet.com/patent on Nov. 21, 2023, 17 pages.
Machine assisted English translation of FR3055214A1 obtained from https://worldwide.espacenet.com/patent on Nov. 21, 2023, 14 pages.
Machine assisted English translation of JPH09241154A obtained from https://worldwide.espacenet.com/patent on Nov. 21, 2023, 10 pages.
Choudhary, M. Iqbal et al., "Effects of ethanolic extract of Iris germanica on lipid profile of rats fed on a high-fat diet", Journal of Ethnopharmacology, vol. 98, No. 1-2, Apr. 1, 2005, pp. 217-220.
Krick, W. et al., "Isolation and Structure Determination of the Precursors of x- and y-Irone and Homologous Compounds from Iris pallida and Iris florentina", Zeitschrift Fuer Naturforschung. C, A Journal of Biosciences, vol. 38, No. 3-4, Apr. 1, 1983, pp. 179-184.
Schutz, Cornelia et al., "Profiling of isoflavonoids in Iris germanica rhizome extracts by microprobe NMR and HPLC-PDA-MS analysis", Fitoterapia, vol. 82, No. 7, Oct. 1, 2011, pp. 1021-1026.
Rahman, Atta Ur et al., "Isoflavonoid Glycosides from the Rhizomes of Iris germanica", Chemical and Pharmaceutical Bulletin, vol. 50, No. 8, Aug. 1, 2002, pp. 1100-1102.

(Continued)

*Primary Examiner* — Qiuwen Mi
(74) *Attorney, Agent, or Firm* — WARNER NORCROSS + JUDD LLP

(57) ABSTRACT

An Orris root extract is disclosed. The Orris root extract is obtained via Orris root materials via selective extraction, and is selectively enriched in (A) a phytochemical melanogenesis stimulating agent or (B) a phytochemical melanogenesis inhibiting agent. The phytochemical melanogenesis stimulating agent (A) comprises germanaism B, and the phytochemical melanogenesis inhibiting agent (B) comprises iriflorental and/or iripallidal. A method of preparing the Orris root extract composition is also provided, and includes selectively extracting an Orris root materials to give at least one Orris root extract. A functional composition comprising the Orris root extract is also provided. The functional composition is adapted for administration to a subject via topical application, and demonstrates activity relating to skin pigmentation.

7 Claims, 6 Drawing Sheets

(56) References Cited

OTHER PUBLICATIONS

Yokosuka, Akihito et al., "Chemical Constituents of the Underground Parts of Iris florentina and their Cytotoxic Activity", Natural Product Communications, vol. 10, No. 6, Jun. 1, 2015.

Machine assisted English translation of WO2012175868A2 obtained from https://worldwide.espacenet.com/patent on Dec. 4, 2023, 34 pages.

Machine assisted English translation of WO20234229A1 obtained from https://worldwide.espacenet.com/patent on Dec. 4, 2023, 6 pages.

Machine assisted English translation of JPH0930954A obtained from https://worldwide.espacenet.com/patent on Dec. 4, 2023, 11 pages.

Machine assisted English translation of JPH0859536A obtained from https://worldwide.espacenet.com/patent on Dec. 4, 2023, 9 pages.

Shiseido Company, Limited, "Shiseido Clarifies "Propagation of Aging" in the Inner Skin—Discovers stem cells inhibiting the propagation of aging are well maintained around sebaceous glands", Press Release, Nov. 2018, 4 pages.

* cited by examiner

Iriflorental
$C_{31}H_{50}O_4$

Iripallidal
$C_{31}H_{50}O_4$

Germanaism B
$C_{23}H_{22}O_{11}$

ORRIS ROOT EXTRACTS, COMPOSITIONS, AND METHODS FOR SKIN APPLICATIONS

CROSS-REFERENCE TO RELATED APPLICATIONS

This application is the U.S. National Stage of PCT/US2022/031882 filed on 2 Jun. 2022, which claims priority to and all advantages of U.S. Provisional Application No. 63/197,132 filed 4 Jun. 2021, the contents of which are incorporated herein by reference in its entirety.

FIELD OF THE INVENTION

The present disclosure relates generally to functional compositions and, more specifically, to Orris root extract compositions useful in altering skin pigmentation, and methods relating to the same.

DESCRIPTION OF THE RELATED ART

Skin pigmentation varies widely in human populations due to the presence of a chemically inert pigment called melanin. The melanin is produced deep inside the skin and deposited in a mosaic manner at the surface of the skin, in which both the amount and distribution of melanin are responsible for skin color variation. Functionally, melanin is essential in protecting skin against ultraviolet (UV) radiation. Specifically, UV-induced reactive oxygen species (ROS) production is well known and linked to DNA damage dermal matrix degradation, which may lead to skin aging or, in some cases, even skin cancer.

Although melanin is critical for providing a self-defense mechanism against such harmful environmental factors, there have also been many studies on regulating the synthesis and transfer of melanin to ameliorate aesthetic problems caused by hyper- or hypo-pigmentation of the skin. The regulation of melanin synthesis (i.e., melanogenesis) is incredibly intricate, yet it has become an important strategy in the global beauty industry leading to development of products that mitigate unwanted skin pigmentation conditions. Melanogenesis takes place in subcellular vesicles called melanosomes produced within melanocytes of the skin. It is believed that over 250 genes are known to be involved in the cascades involved in melanogenesis, along with a variety of proteins and cofactors. For example, microphthalmia induced transcriptional factor (MITF), a melanocyte-specific transcription factor that is known as a master regulator of melanogenesis is controlled by numerous cascades of signaling pathways such as α-MSH/MCIR, Wnt/b-catenin and SCF/c-Kit (ERK signaling pathway). MITF has been reported to up-regulate Tyrosinase (TYR) expression, with TYR having been established as a rate-limiting enzyme in the formation of melanin, where it controls the process of oxidation and polymerization of tyrosine along with TYR Related Protein 1 and 2.

Commercial interest in skin pigmentation has led to markets in the cosmetics industry for both skin lightening and darkening products. Skin darkening is often desirable to improve appearance or provide more even skin tone. Tanning is a more commonly used process in which skin darkening is increased through exposure to UV radiation from sunlight. However, long term exposure to UV light can result in accelerated signs of skin aging and increased risk of skin cancer as noted above. Therefore, the ability to generate darker skin tone without incurring photo-damage has led to development of cosmetic and "self-tanning" applications. As such, DHA (Dihydroxyacetone)-based products or temporary bronzers have been developed as topical tanners that are applied to the skin to give the appearance of a tan without involving underlying skin pigmentation. Alternative approaches such as stimulating inner skin pigmentation by targeting melanogenesis pathways have also taken place using synthetic or natural agents. For instance, afamelanotide, a synthetic α-MSH analog, induces melanin production via activation of α-MSH/MCIR pathway. A number of salt-inducible kinase (SIK) inhibitors have also been found to stimulate melanogenesis by amplifying MITF expression and its target TRPM1 independent from α-MSH/MCIR activation. Forskolin and synthetic reagents such as isobutylmethylxanthine (IBMX) are known to regulate adenylyl cyclase and phosphodiesterases, respectively inducing downstream of α-MSH/MCIR pathway, resulting in an increase in melanin biosynthesis. Many darkening agents have been isolated from numerous plant sources such as *Glycyrrhiza glabra, Vigna angularis*, citrus plants, etc., which induce melanogenesis by stimulating melanogenic protein expression and pathways in both in vitro or in vivo systems.

Skin lightening products are commercially available for cosmetic purposes to obtain lighter skin complexion and are also used to treat hyper-pigmentary disorders such as melasma, dark spot, and solar lentigo. As skin pigmentation is mainly determined by the content of melanin in melanosomes and the distribution of melanosomes in keratinocytes, the down-regulation of melanogenesis and melanosome transfer to keratinocytes are often contemplated as primary targets for skin lightening agents. Since the establishment of TYR as the rate limiting enzyme in melanogenesis, it has become the most prominent and successful target for melanogenesis inhibitors and lead to use of hydroquinone, L-ascorbic acid, kojic acid, arbutin, azelaic acid, ellagic acid, tranexamic acid, and resorcinol derivatives as skin lightening agents. Other avenues for skin lightening have also been pursued. For example, α-Viniferin and diacetylcaffeic acid cyclohexyl ester (DACE) are known to decrease melanin levels by targeting α-MSH/MCIR pathway, independent from affecting TYR activity directly. In addition, as the transfer of mature melanosomes into keratinocytes is another critical factor in skin pigmentation, melanosome transfer inhibitors such as protease-activated receptor 2 (PAR-2) inhibitors, niacinamide, and cytidine have been studied and demonstrate skin lightening effects without impacting melanin synthesis.

BRIEF SUMMARY

An Orris root extract (the "extract") is provided. The extract is obtained from Orris root and selectively enriched in (A) a phytochemical melanogenesis stimulating agent or (B) a phytochemical melanogenesis inhibiting agent. In some embodiments, the phytochemical melanogenesis stimulating agent (A) comprises germanaism B. In these or other embodiments, the phytochemical melanogenesis inhibiting agent (B) comprises iriflorental and/or iripallidal.

A method of preparing the extract (the "preparation method") is also provided. The method comprises drying an Orris root material to give a dried Orris root feedstock, and selectively extracting the dried Orris root feedstock with a concerted solvent system to give the Orris root extract, which is selectively enriched in the phytochemical melanogenesis stimulating agent (A) or the phytochemical melanogenesis inhibiting agent (B). In some embodiments, extracting comprises a two-stage hydroethanolic extraction that prepares a first and second extract, with the first extract being enriched in the phytochemical melanogenesis stimulating agent (A) and the second extract being enriched in the phytochemical melanogenesis inhibiting agent (B).

A topical composition comprising the extract is also provided. The topical composition may be utilized in personal care or other products to elicit a skin and/or hair darkening (e.g. tanning) or lightening effect in a subject after application.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE INVENTION

Figures 1, 2:
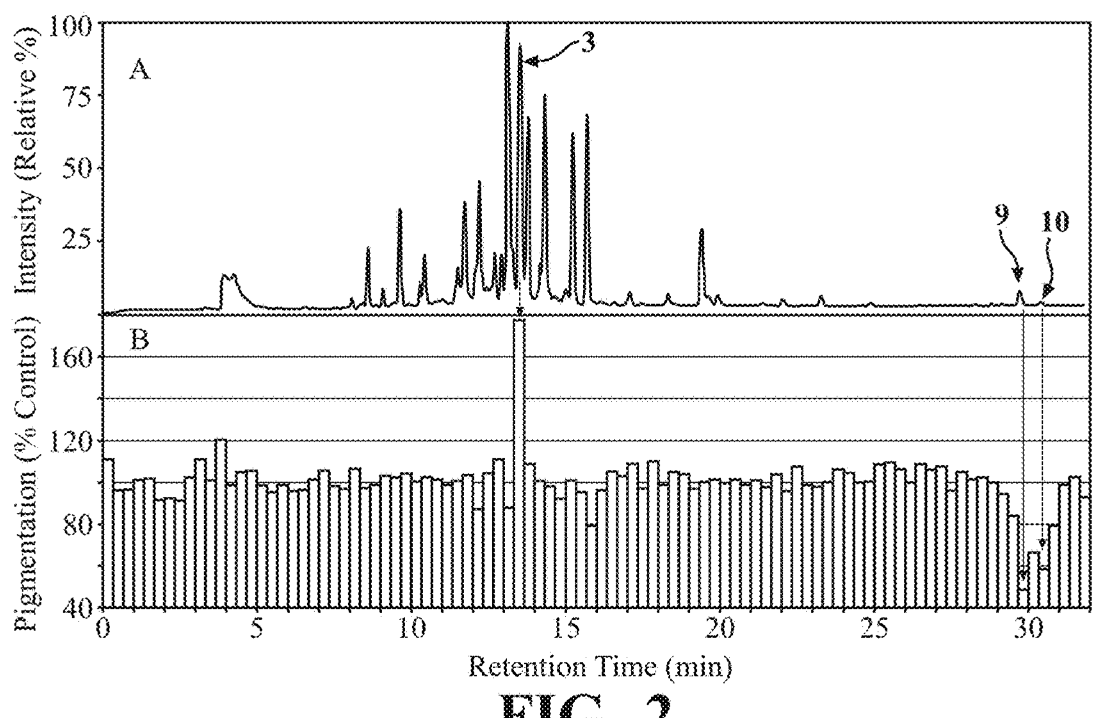
FIG. 1 provides the chemical structures of phytochemicals extracted from Orris root material.
FIG. 2 shows the results of a Bioassay Directed Fractionation (BDF), via LC-MS.

The present disclosure provides an Orris root extract (the "extract"), as well as functional compositions and methods of preparing each of the same. In general, the extract comprises one or more phytocompounds discovered to alter skin pigmentation and/or appearance. Specifically, it is believed that particular phytocompounds in the extract, which are described below, may act on the melanogenesis pathway to affect melanin production and thus the visual lightness/darkness of skin and/or hair appearance. As such, the extract may be utilized in topical compositions adapted for skin and/or hair lightening or darkening (e.g. tanning).

As will be understood from the description herein, in various embodiments the extract is prepared in a selective process (the "preparation method") that utilizes a creative extraction with two different solvent systems used sequentially on the same feedstock, providing a unique avenue to obtaining two different extracts with very different—and contrasting—biological/practical effects via selective enrichment of a melanogenesis stimulating agent and depletion of a melanogenesis inhibiting agent, or vice versa. The preparation method therefore provides for improved resource economy by generating two different functional components from one starting material. Moreover, it is believed that the preparation method, as well as the extracts prepared therewith, provide the first use of the phytochemical melanogenesis stimulating agent germanaism B to affect the melanogenesis effects of a composition, as well as an Orris root extract demonstrates skin darkening effects when applied to a subject. As such, in contrast with conventional Orris root extracts known and utilized for irone composition and content, it is to be appreciated that the present embodiments are unique in the use of germanaism B, as well as the relative proportions of germanaism B to certain iridals, to tailor the skin darkening or lightening properties of a novel Orris root extract.

Extract

As used herein in the context of the extract, functional compositions, and related embodiments, the term "extract" is to be understood in the ordinary and customary sense, i.e., as a substance obtained by extracting a material using a solvent system or equivalent process. Examples of extracting processes (i.e., "extractions") include hot solvent extractions, supercritical fluid extractions (SFE) such as fractional supercritical fluid extraction (FSFE), etc., which are described in further detail below. In this same context, the term "Orris root" is used herein to refer generally to particular parts of plants of the family Iridaceae, including *Iris germanica* L. (i.e., "bearded iris"), *Iris florentina* L. (i.e., "Florentine iris" or "Glaive lily"), and *Iris pallida* L. ("Dalmatian iris" or "sweet iris"), with the term "Orris root" including the lower part(s) of the plant that naturally present below, into, and/or sometimes on the surface of the ground. In this sense, it is to be understood that the Orris root extract may be prepared from any part of the relevant plants, including rhizomes, roots, stems, rootstalks, etc., which will be readily appreciated by those of skill in the art in view of the description below. Typically, the extract is obtained from the rhizome of an Iris plant (i.e., rhizoma iridis) via extraction techniques, which are described in further detail below.

In view of the above, it will be understood that the term "Orris root extract" used herein refers to a substance generally obtained via extraction of an Orris root material (i.e., a material comprising or consisting of a root part of an Iris plant). As understood in this specification, "root" is any portion of a plant that is typically mostly underground. This definition includes rhizomes. However, it will be appreciated that the substance of the extract in the present embodiments encompasses forms that may be more specifically described as "isolates," "distillates," "concentrates," etc. As such, while the term "extract" may possess a specific meaning with regard to a particular product, it is to be understood that, in the context of the disclosure herein, the term "Orris root extract" and corresponding reference to "the extract" is to be interpreted broadly in view of the description and examples below.

Phytocompounds

The extract comprises, alternatively consists essentially of, one or more phytocompounds obtained or otherwise derived from the Orris root material. As will the understood by those of skill in the art, phytocompounds, which may also be referred to generally as "phytochemicals," are chemical entities that are found in or derived from plants, and thus represent a diverse group of substances that vary widely in terms of structure, form, and biological activity in non-plant organisms. For example, certain phytocompounds may be classified as macromolecular, polymeric, low molecular weight, or small molecules. Many phytocompounds are not bioactive with respect to certain biological processes, e.g. due to being non-digestible, poorly bioavailable, and/or otherwise recalcitrant or inert with respect to particular biological targets. Other phytocompounds, however, are bioactive and may therefore be exploited in functional compositions, as described in further detail below. Some specific classifications of phytocompounds are also known in the art and based upon a particular characteristic or property, such as phytotoxins (i.e., phytocompounds toxic to humans and/or other species), antinutrients (i.e., phytocompounds that interfere with the absorption of nutrients in a host), etc. Owing to such diverse activity and related effects, and as described in further detail below, the specific phytocompounds, or limited group of phytocompounds, in the extract may be advantageously employed in various ways that are not practical, effective, or even possible with the Orris root material from which they are obtained (i.e., extracted).

In general, phytocompounds that may be present in the extract include terpenes, terpenoids, flavonoids, phenolics, glycosides, and alkaloids, as well as derivatives thereof, as will be appreciated in view of the further description and examples herein. Three specific phytocompounds, germanaism B, iripallidal, and iriflorental are shown in FIG. 1 and described in turn below.

Germanaism B

In certain embodiments, the extract comprises (A) a phytochemical melanogenesis stimulating agent. In such embodiments, the extract typically exhibits skin-darkening effects and may thus be utilized as a component of a skin darkening composition, such as the topical composition described below. It will be appreciated that the term "stimulating" in this context is not limited, and may encompass promotion of melanogenesis, inhibition of a competing/regulatory pathway, or both. In this sense, the term "melanogenesis stimulating agent" is used descriptively to refer to an overall effect of melanogenesis and/or skin pigmentation involving melanin, but may also be used more specifically regarding particular biological pathways where indicated.

Typically, the phytochemical melanogenesis stimulating agent (A) comprises, alternatively consists essentially of, alternatively is, germanaism B (CAS #123648-56-6; alternatively known as "irisolone 4'-O-beta-D-glucoside" and "nigricin 4'-O-beta-D-glucoside"). As demonstrated in the examples below, germanaism B is effective to increase pigmentation via effect(s) on melanin-related biological pathways.

Iridals

In certain embodiments, the extract comprises (B) a phytochemical melanogenesis inhibiting agent. In such embodiments, the extract typically exhibits skin-lightening effects and may thus be utilized as a component of a skin lightening composition, such as the topical composition described below. It will be appreciated that the term "inhibiting" in this context is not limited, and may encompass direct inhibition of melanogenesis, promotion of a competing/regulatory pathway, or both. In this sense, the term "melanogenesis inhibiting agent" is used descriptively to refer to an overall effect of decreasing melanogenesis and/or skin pigmentation involving melanin, but may also be used more specifically regarding particular biological pathways where indicated.

Typically, the phytochemical melanogenesis inhibiting agent (B) comprises one or more irone precursors known as "iridals". Examples of such iridals include the bicycloiridals iripallidal and iriflorental. In certain embodiments, the phytochemical melanogenesis inhibiting agent (B) consists essentially of, alternatively is, iripallidal and/or iriflorental.

Selective Enrichment

It will be appreciated that the phytochemical melanogenesis affecting agents (A) and (B) (e.g. as exemplified by germanaism B and the iridals iripallidal and iriflorental, respectively) poses conflicting activity in the context of melanogenesis. As such, as described and exemplified further below, the extract comprises a predominant amount of but one of these phytochemical melanogenesis affecting agents. Specifically, in certain embodiments, the extract is selectively enriched in the phytochemical melanogenesis stimulating agent (A). In some such embodiments, the extract is selectively depleted in the phytochemical melanogenesis inhibiting agent (B). In other embodiments, the extract is selectively enriched in the phytochemical melanogenesis inhibiting agent (B). In some such other embodiments, the extract is selectively depleted in the phytochemical melanogenesis stimulating agent (A). The terms "enriched" and "depleted" in this context may be understood to be in reference to the Orris root material from which the extract is obtained. Said differently, the extract may be "enriched" with respect to phytochemical (A) by containing a higher proportion of the phytochemical (A) than the Orris root material, a lower proportion of compounds other than the phytochemical (A) as compared to the Orris root material, or both. The same is true for being enriched or depleted in terms of phytochemical (B), which proportion may also refer to the relative amounts and/or overall concentration of the phytochemical in the Orris root material. In this fashion, the extract comprises a predominant amount of the desired melanogenesis affecting agent (i.e., phytochemical (A) or (B)), and thus may demonstrate a biological effect/activity not possible with the raw Orris root material, or even an extract comprising phytochemicals (A) and (B) in similar proportions as found in such Orris root material.

Other Phytocompounds

The extract may be enriched with one or more desired phytocompounds, i.e., other than phytochemical (A) or (B), relative to the concentration of such phytocompounds in the Orris root material. Additionally, the extract may contain a lower concentration of unwanted materials, including certain phytocompounds (e.g. particular terpenes, alkaloids, waxes, acids, etc.), as compared to the Orris root material. For example, in some embodiments, the extract is substantially free from, alternatively is free from, iriflorentin.

Form of Extract

The form of the extract is not particularly limited, and will be selected by those of skill in the art, e.g. based on the particular techniques and materials used in the preparation method, as described below. In general, the extract may be a direct extract, such as a solvent-based composition obtained from a solvent-based extraction process or, alternatively, a processed form of such an extract (e.g. prepared via removal of solvent and/or additional processing/formulation steps). In this fashion, the extract may be further defined, or otherwise characterized, as an oil or essential oil, a tincture, a concentrate, an isolate, a distillate, or the like, or combinations thereof, based on the particular techniques utilized in the preparation method. Such characterizations may be based on colloquial or common usage of the terms, based on art-specific usage of the terms, or both, e.g. where a "tincture" in this context may refer generally to a solvent extract of plant material, a solution of such an extract, and/or of a low volatility substance obtained from such an extraction. Similarly, the terms "concentrate" and "essential oil" may both be used in the context of the extract to refer to a substance obtained by extracting a plant material with using a solvent, and subsequently removing, or mostly removing the solvent. In certain instances, the extract may be defined or otherwise characterized based on a regulatory definition. For example, in certain embodiments the extract may be prepared from sanitized rhizomes that are substantially free from other plant material, and fall within the bounds of regulatory guidelines for Orris root extracts.

It will be understood that certain forms of the extract, such as those introduced herein, may overlap with one another with regard to production methods, state-specific properties, intermediate forms, etc. For example, a tincture prepared via hot solvent extraction of Orris root material may be concentrated or distilled to prepare a concentrate or essential oil. In certain embodiments, the extract is prepared via one or more post-extraction processes, which may be characterized as a purification process. In the context of the extract, such purification processes may be employed to remove or reduce a substance from the composition being purified, or remove a desired substance (i.e., the extract) from a mixture of substances obtained from the Orris root material. Examples of substances that may be removed include waxes, pigments, oils, terpenes, alkaloids, and even portions of plant biomass that is not dissolved in the solvent system utilized in the extraction process. As such, example of purification techniques that may be employed include, distillation, concentration, filtration, chromatography, fractionation, isolation, secondary extraction, and the like, as well as combinations thereof. In this fashion, it will be appreciated that the extract can be selectively enriched with particular phytocompounds, including the phytochemical melanogenesis stimulating agent (A), the phytochemical melanogenesis inhibiting agent (B), as well as other phytochemicals present in the Orris root material. Likewise, the extract may contain lower concentrations of any such phytochemicals that are undesirable in a particular formulation of a desired final composition.

Preparation Method

As introduced above, the preparation method gives the extract from an Orris root material. Typically, the Orris root material comprises, alternatively is, the rhizome of an Iris plant. However, it will be appreciated that other parts or materials from an iris plant (e.g. hairy roots, stems, leaves, etc.) may also be utilized in the preparation method. Such other materials may be combined with the Orris root material prior to or during pre-extraction processing of the Orris root material, the extraction process itself, or post-extraction processing. In general, the Orris root material utilized in the preparation method may be prepared, purchased, or otherwise obtained.

In some embodiments, the preparation method comprises preparing the Orris root material for extraction (i.e., pre-extraction processing). In such embodiments, techniques that may be employed include cutting, grinding, soaking, blending, sifting, milling, drying, desiccating, and the like, as well as combinations (e.g. via sequential use) thereof. In certain embodiments, a chemical process (e.g. initiated via heating, acidification, oxidation, etc.) may be used to modify one or more substances in the Orris root material in order to increase or alter the efficacy of a subsequent extraction step. Likewise, various purification techniques (e.g. screening, filtration, chromatography, etc.) may be utilized with such processes before and/or after individual steps or sequences.

Pre-Extraction Processing

For example, in particular embodiments, preparing the Orris root material for extraction comprises harvesting iris plants and isolating rhizomes from the harvested iris plants (e.g. by removing hairy roots and/or other parts of the iris plant therefrom). In other embodiments, the harvested iris plants are used whole, or partially whole, in the extraction step, i.e., without removal of hairy roots or certain plant parts therefrom. In various embodiments, preparing the Orris root material may also comprise washing the harvested iris plants and/or the rhizomes isolated therefrom, e.g. to remove dirt and debris before further processing. In some such embodiments, washing may comprise sanitizing the iris plant material, e.g. via soaking the rhizomes and/or other harvested plant parts in a sterilizing and/or sanitizing solution.

In some embodiments, preparing the Orris root material comprises a drying process in order to provide the Orris root material with a particular moisture content ahead of the extraction steps. For example, in certain embodiments the preparation method comprising drying washed rhizomes by exposure to ambient air and temperature (i.e., air drying). In some embodiments, however, an oven or other such drying device may be utilized to forcibly remove or drive moisture from the plant material. For example, in some embodiments, preparing the Orris root material comprises oven drying rhizomes to a moisture content of less than 15 wt. % by weight, such as from 5 to 15, alternatively from 6 to 12, alternatively from 8 to 10, wt. %, based on the weight of the Orris root material. In such embodiments, the Orris root material may be resized to aid in drying or other processing steps. For example, in certain embodiments, preparing the Orris root material comprises milling dried rhizomes to prepare a powder therefrom. In such embodiments, the Orris root powder may be used directly in the extraction process. Alternatively, the Orris root powder may be processed for medium to long-term storage, e.g. via freezing.

It will be appreciated that variations on the pre-extraction processing of the Orris root material may be employed without deviating from the scope of the present embodiments. For example, alternatively sizing steps such as chopping, dicing, cubing, etc., may be used in addition or as an alternative to the milling described above, to prepare the Orris root material in various forms different in homogeneity, average particle size, surface area, etc. Such properties may be altered depending on the size/scale of the processing and/or extraction being carried out, as will be understood by those of skill in the art. For example, harvested Orris root material may be rough-cut (e.g. via chopping) to aid in washing/soaking/drying/etc., and the eventual dried product still milled or ground to give the Orris root powder for extraction. Alternatively, such rough-cut forms may be dried and extracted directly.

Extraction

As introduced above, the preparation method involves a selective extraction process that utilizes two different solvent systems sequentially on the same feedstock (i.e., the Orris root material) to give two different Orris root extracts. Specifically, a first extraction is utilized to prepare a first extract and an extracted feedstock from the Orris root material, and a second extraction is utilized to prepare a second extract from the extracted feedstock. The extraction sequence, and particular features of the first and second extractions, are described further below.

In general, the preparation method utilizes a solvent-based extraction process. Said differently, the extraction steps of the preparation method are carried out using solvent-based extraction techniques known in the art. As such, the specific techniques utilized in each extraction are not particularly limited, and may be adjusted and/or replaced by alternative extraction techniques suitable for preparing the extracts described herein. That said, it will also be appreciated that certain limitations may apply to the conditions utilized during the extractions, as well as on the pre-extraction processing steps described above. For example, steam distillation of Orris root material is known to oxidize iridals and give various fragrance phytochemicals, such as irones. While such irones may sometimes be desired in the extract or final products containing the same, such oxidation depletes the available amount of iridals for extraction, and thus may be avoided in certain embodiments. In particular embodiments, the preparation method is carried out under conditions selected to reduce, alternatively minimize, the oxidation or chemical/thermal degradation of the target phytochemicals (e.g. germanaism B, iridals, etc.) being extracted from the Orris root material.

Extraction Solvent

Figure 8:
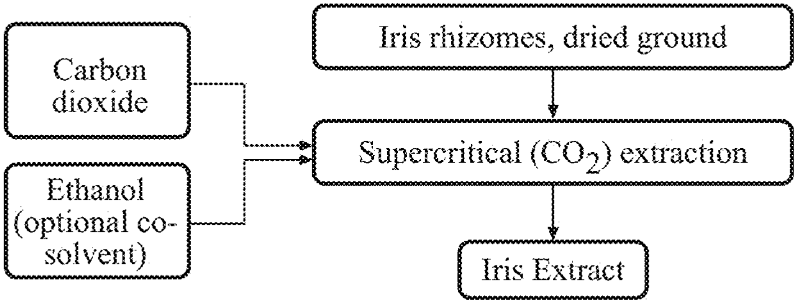
FIG. 8 shows a flow chart of one embodiment of a method of preparing an Orris root extract via supercritical fluid extraction (SCFE) with $CO_2$.

The solvent system utilized in the extraction step will be selected to dissolve or suspend the desired phytocompounds present in the Orris root material, and thus will be selected based on the solubility of the various phytocompounds therein. In general, solvents suitable for use in the extraction steps of the preparation method comprise aqueous and/or water compatible solvents. Examples of such solvents, or components of suitable solvent systems, generally include water (e.g. purified, deionized, etc.); certain organic solvents such as alcohols (particularly lower alcohols such as methanol, ethanol, etc.), glycols (such as propylene glycol, pentylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); and the like, as well as derivatives, modifications, and combinations thereof. Other organic solvents that may be utilized in addition to those above include acetone, tetrahydrofuran, ethyl acetate, chloroform, methylene chloride, diethyl ether, and hexane. Other solvent types may also be utilized. For example, in certain embodiments, supercritical $CO_2$ is utilized to extract the Orris root material. In some embodiments, supercritical $CO_2$ is utilized in conjunction with an optional ethanol co-solvent as shown in FIG. 8.

Notwithstanding the above, it will be appreciated that the solvent(s) selected for use in the preparation method must be capable of carrying the desired phytocompounds from the Orris root material. Moreover, as will be understood from the additional description herein, the solvent(s) utilized will also determine the relative concentration of phytochemical melanogenesis stimulating agent (A) and/or phytochemical melanogenesis inhibiting agent (B) obtained from the Orris root material. As such, certain solvents may not be widely applicable. For example, in certain embodiments, pure-water extraction (i.e., the use of water alone) may not extract enough of the desired phytocompounds from the Orris root material to prepare extracts suitable for use in the functional composition described herein. More specifically, the desired phytocompounds are typically not polar enough to be isolated from the Orris root material by water alone, but may instead require a non-polar solvent be used in conjunction with the water for successful extraction.

As the desired phytocompounds differ with respect to one another in terms of polarity, the preparation method typically utilizes different solvent systems to selectively prepare extractions enriched in the phytochemical melanogenesis stimulating agent (A) or phytochemical melanogenesis inhibiting agent (B). As introduced above, the preparation method typically utilizes sequential extractions, each with a different solvent system, in order to prepare two separate extracts from the Orris root material. Illustrative embodiments are exemplified by the flow diagrams of the preparation method shown in FIGS. 5-8.

In some embodiments, the preparation method utilizes hydroethanolic solvent system for the extraction steps. More specifically, in such embodiments, the extraction solvent comprises a mixture of ethanol (EtOH) and water ($H_2O$).

First Extraction

As introduced above, in general embodiments, the preparation method includes performing a first extraction on the Orris root material to give a first extract and an extracted feedstock therefrom. Typically, the first extraction utilizes a hydroethanolic solvent system, e.g. a solvent system comprising, alternatively consisting essentially of, a mixture of ethanol (EtOH) and water ($H_2O$). For example, in some embodiments, the first extraction utilizes a hydroethanolic solvent system comprising ethanol and water in a relative ratio of from greater than 0 to 50% ethanol in water, e.g. from 5 to 40, alternatively from 10 to 35, alternatively from 10 to 20, % ethanol in water. In specific embodiments, the first extraction solvent is a hydroethanolic solvent system comprising ethanol and water in a ratio of about 15:85 ($EtOH:H_2O$). It will be appreciated that these exemplary ranges are illustrative of the hydroethanolic solvent system employed, and alternative ranges may be selected based on the particular solvents in any given solvent system as well as the desired extract being prepared. However, the first solvent system is generally selected to be more polar than the second extraction, i.e., to extract relatively more polar components from the Orris root material. More specifically, in certain embodiments, the first extract comprises the phytochemical melanogenesis stimulating agent (A), exemplified by germanaism B, which is differentially extracted on the basis of increased polarity over the phytochemical melanogenesis inhibiting agent (B), as exemplified by the iridals iriflorental and iripallidal. As such, the first extract is typically enriched with respect to the content of the phytochemical melanogenesis stimulating agent (A), and depleted with respect to the content of the phytochemical melanogenesis inhibiting agent (B), as compared to the Orris root material utilized in the preparation method.

With the regard to the first extraction, any suitable technique may be utilized to obtain the first extract therefrom. Typically, the first extraction comprises heating and agitating a mixture of a first extraction solvent and the Orris root material. For example, in some embodiments, the first extraction comprises combining together the first extraction solvent and the Orris root material to give a first extraction mixture, and then agitating the first extraction mixture (e.g. via stirring, etc.) to facilitate the extraction process. In these or other embodiments, the first extraction further comprises heating the first extraction mixture.

When heating is employed, it is to be appreciated that conservative temperatures are typically utilized in order to avoid undesired oxidation and/or chemical or thermal degradation of the desired phytocompounds in the Orris root material being extracted, as well to protect the extracted phytocompounds once solubilized in the mobile phase of the extraction. As such, the temperature of the first extraction is typically bounded on the upper end by the reflux temperature of the solvent system being utilized. However, temperatures suitable for rupturing, compromising, or breaking down the plant cell walls of the Orris root material will typically be employed to increase the efficiency of the extraction. Likewise, the viscosity of the soluble components of the first extraction mixture will also be considered when selecting an appropriate temperature, as lowering the viscosity of desired phytochemicals will generally increase the diffusion, and thus extractability, thereof. In specific embodiments, the temperature of the first extraction is maintained within a range of from greater than room temperature to 70° C., such as from 30 to 65, alternatively from 40 to 65, alternatively from 50 to 65, alternatively of about 60, ° C.

The mixture of the first extraction solvent and the Orris root material may be selected to control the relative proportion of solvent to Orris root material therein. For example, in certain embodiments, the first extraction is carried out at a ratio of around 10:1 parts by weight solvent to Orris root material. It will be appreciated that ratios outside this range may also be utilized. However, reduced yields may be obtained when the mixture is too concentrated (e.g. below 6-8:1 parts by weight solvent to Orris root material), and waste is generated when the mixture is too dilute such that excess solvent need be utilized. That said, in some embodiments, an excess, alternatively a gross excess, of solvent may be utilized.

The first extraction may be carried out for any time period suitable for extracting the desired phytocompound(s) from the Orris root material. For example, in some embodiments, the first extraction comprises agitating the mixture of Orris root material and the hydroethanolic solvent within the temperature ranges above for a duration of from 30 minutes to 4 hours, such as from 1 to 3, alternatively of about 2, hours. Of course, longer durations may also be employed, such as when the Orris root material is not processed prior to the first extraction, the scale of the first extraction is relatively large, the temperature is maintained at the lower end of the preferred ranges, a lower proportion of the first extraction solvent is utilized, etc.

It will be appreciated that the first extraction prepares a mixture comprising an extracted/intermediate Orris root material (e.g. solids) and the solvent system employed in the first extraction, with the latter also comprising the extracted phytocompounds. Typically, the first extraction process includes a filtration step or similar technique to separate the phases of the mixture, thereby giving a first extract (i.e., as the filtrate) and the extracted Orris root feedstock (i.e., the filtrand). In particular embodiments, the first extraction process of the preparation method comprises cooling and filtering the first extraction mixture, e.g. through a mesh, to separate and independently obtain the first extract and the extracted Orris root feedstock.

Figure 6:
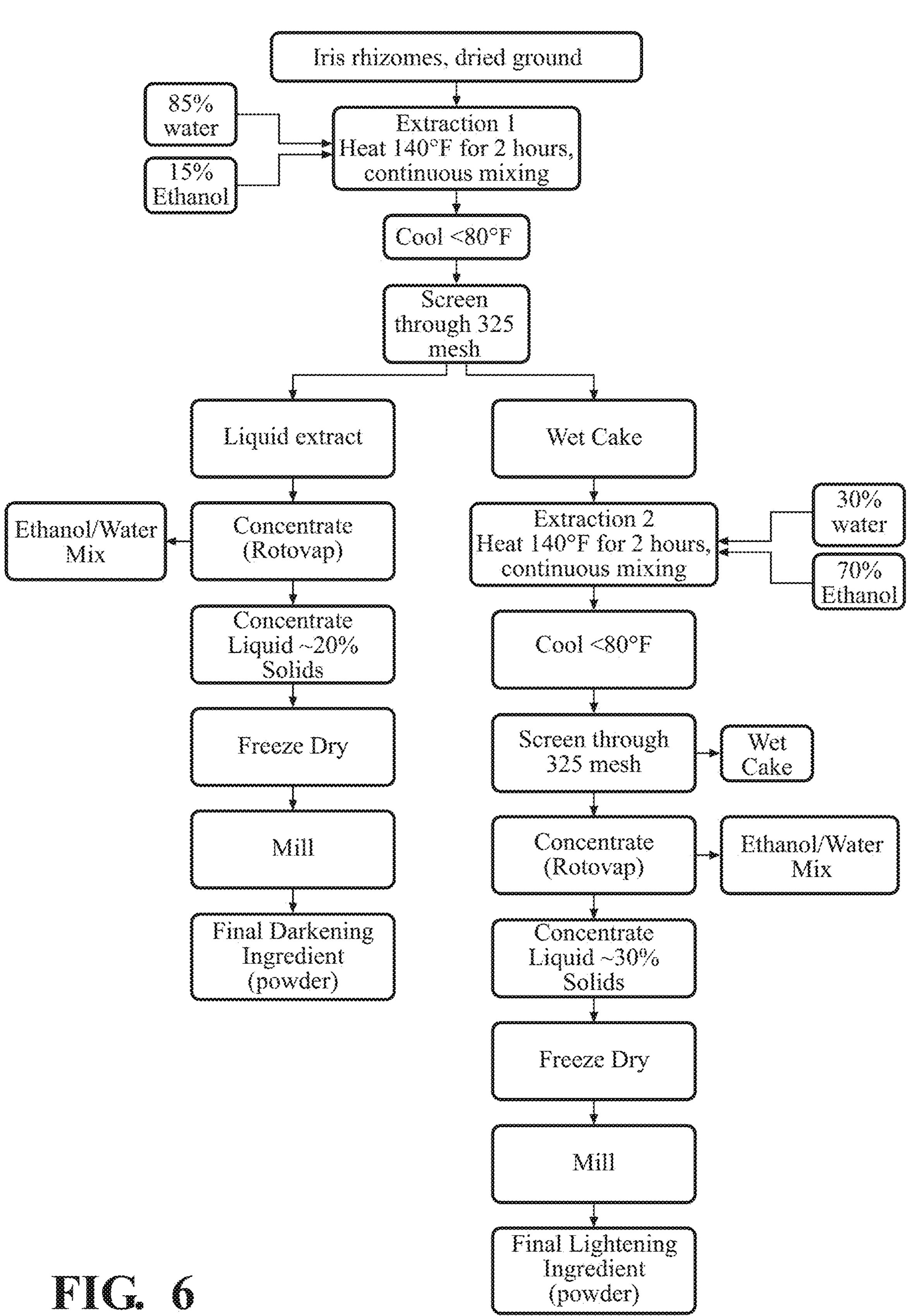
FIG. 6 shows a flow chart of another embodiment of a method of preparing an Orris root extract.
Figure 7:
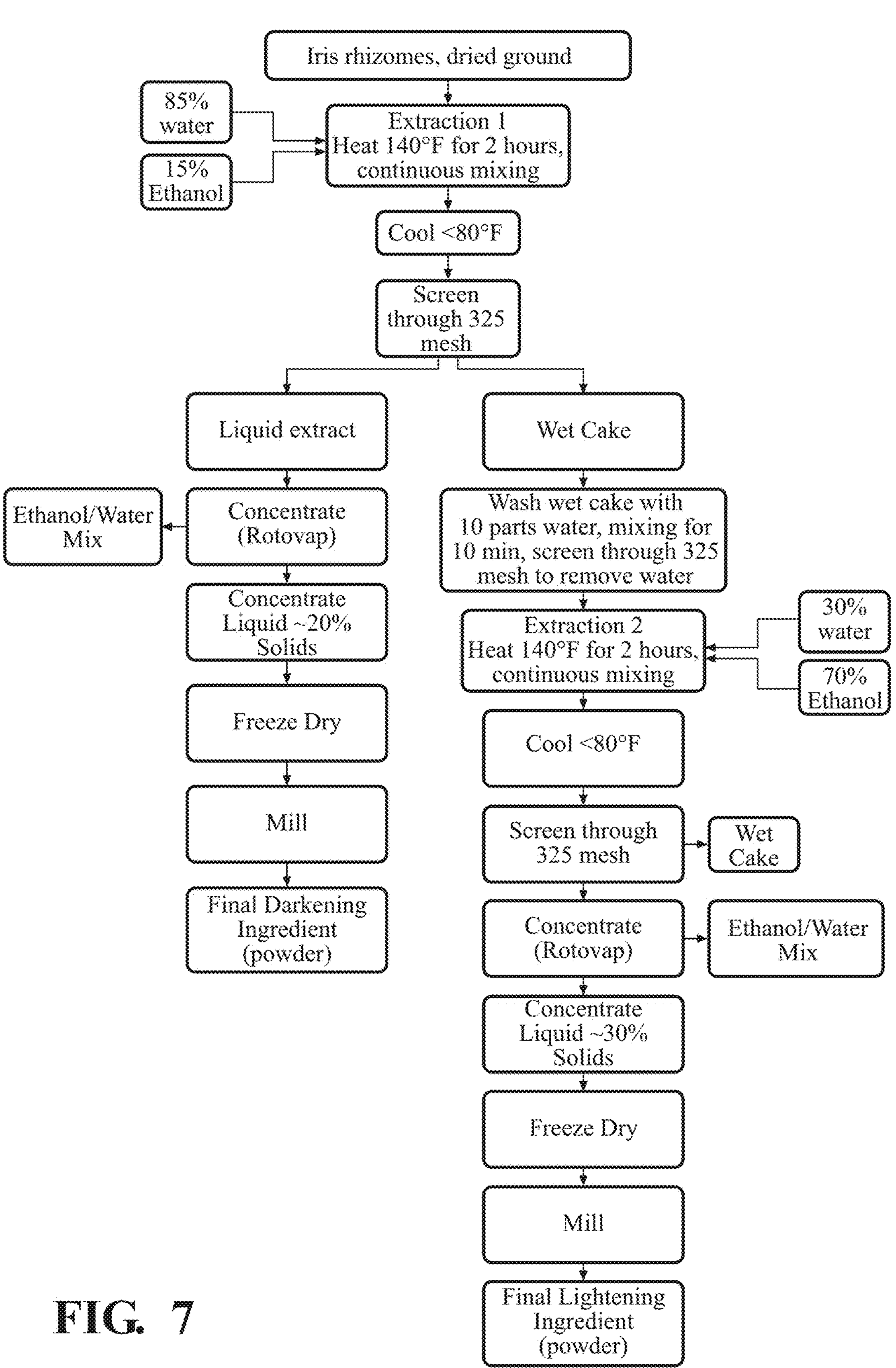
FIG. 7 shows a flow chart of a further embodiment of a method of preparing an Orris root extract.

As introduced above, the first extract generally comprises the phytochemical melanogenesis stimulating agent (A), exemplified by germanaism B. As such, once obtained, the first extract may be used directly in the formulation of a functional composition, such as those described below for skin darkening applications, or may instead be subjected to post-extraction processing to give a final first extract composition. For example, in some embodiments, the filtrate obtained after the first extraction and post-extraction filtration is concentrated to remove all or some of the extraction solvent therefrom and give the first extract as a concentrate. The particular concentration process is not particularly limited, and the final amount of solvent/solids in the first extract may be independently selected, e.g. based on a desired end-use thereof. For example, in certain embodiments, the first extract is concentrated to reach a final solids content in the range of from 15 to 25%, such as about 20% total solids. Of course, the final concentration of the phytochemical melanogenesis stimulating agent (A) (e.g. germanaism B) may vary, and may be readily determined by one of skill in the art via myriad known analytical techniques, such as those illustrated in the examples herein. In certain embodiments, the first extract, in the form of the concentrate, is freeze dried and milled to obtain the first extract as a powder (e.g., as shown in FIGS. 6 and 7).

Second Extraction

The extracted/intermediate Orris root feedstock obtained from the first extraction may be further extracted with a second extraction solvent system, i.e., in a second extraction step of the preparation method. Importantly, based on the differential extraction utilized between the first and second extractions, it will be appreciated that the extracted Orris root feedstock will generally be depleted in terms of the content of the phytochemical melanogenesis stimulating agent (A) therein, such that the second extract will also contain significantly reduced amounts of that phytocompound in comparison to the Orris root material used in the first extraction. Conversely, the second extract is typically enriched with respect to the content of the phytochemical melanogenesis inhibiting agent (B), and depleted with respect to the content of the phytochemical melanogenesis stimulating agent (A), as compared to the Orris root material utilized in the preparation method. In this fashion, the preparation method utilizes the sequential extractions to prepare two separate extracts from a single feedstock material, with each extract comprising phytocompounds with different melanogenesis-related activity.

The preparation method may comprise one or more processing steps between the extractions in order to prepare or condition the Orris root material for the second extraction. For example, in certain embodiments, the extracted/intermediate Orris root material is obtained as a cake from the filtration step following the first extraction, and the preparation method comprises washing or suspending the cake (e.g. with 5-15, alternatively 10 parts water) and filtering the suspension to remove the washing solvent and give the extracted/intermediate Orris root as a feedstock for the second extraction. Some illustrative examples of such steps are shown in the processes depicted in FIGS. 5-7.

With regard to the second extraction, the description above regarding techniques and solvents relative to the first extraction is generally equally applicable. However, the second extraction solvent is typically less polar than the first extraction solvent, due to the differing polarities of the desired phytocompound(s) (i.e., the phytochemical melanogenesis inhibiting agent (B)) being extracted. For example, in some embodiments, the second extraction utilizes a hydroethanolic solvent system comprising ethanol and water in a relative ratio of from 50 to 100% ethanol in water, e.g. from 60 to 80, alternatively from 65 to 75, alternatively from 70 to 75, % ethanol in water. In specific embodiments, the second extraction solvent is a hydroethanolic solvent system comprising ethanol and water in a ratio of about 70:30

($EtOH:H_2O$). It will be appreciated that these exemplary ranges are illustrative of the hydroethanolic solvent system employed, and alternative ranges may be selected based on the particular solvents in any given solvent system as well as the desired extract being prepared. However, the second solvent system is generally selected to be less polar than the first extraction, i.e., to extract relatively less polar components from the Orris root material as compared to the first extraction. More specifically, in certain embodiments, the second extract comprises the phytochemical melanogenesis inhibiting agent (B), exemplified by the iridals iriflorental and iripallidal. As such, the second extract is typically enriched with respect to the content of the phytochemical melanogenesis inhibiting agent (B), and depleted with respect to the content of the phytochemical melanogenesis stimulating agent (A), as compared to the Orris root material utilized in the preparation method.

In certain embodiments, the second extraction is carried out at a ratio of around 10:1 parts by weight solvent to extracted/intermediate Orris root material. It will be appreciated that ratios outside this range may also be utilized. However, as with the first extraction reduced yields may be obtained when the mixture is too concentrated (e.g. below 6-8:1 parts by weight solvent to extracted/intermediate Orris root material), and waste is generated when the mixture is too dilute such that excess solvent need be utilized and subsequently removed. That said, in some embodiments, an excess, alternatively a gross excess, of the second extraction solvent may be utilized.

The temperature of the second extraction typically maintained within a range of from greater than room temperature to 70° C., for the reasons described above with respect to the first extraction. As such, in some embodiments, a temperature of from 30 to 65, alternatively from 40 to 65, alternatively from 50 to 65, alternatively of about 60, ° C., is utilized.

The second extraction may be carried out for any time period suitable for extracting the desired phytocompound(s) from the extracted/intermediate Orris root material. For example, in some embodiments, the second extraction comprises agitating the mixture of the extracted/intermediate Orris root material and the second hydroethanolic solvent within the temperature ranges above for a duration of from 30 minutes to 4 hours, such as from 1 to 3, alternatively of about 2, hours. Of course, longer durations may also be employed.

It will be appreciated that the second extraction prepares a mixture comprising a spent Orris root material and the solvent system employed in the second extraction, with the latter also comprising the extracted phytocompounds. Typically, the second extraction process includes a filtration step or similar technique to separate the phases of the mixture, thereby giving a second extract (i.e., as the filtrate) and the spent/extracted Orris root material (i.e., the filtrand). In particular embodiments, the second extraction process of the preparation method comprises cooling and filtering the second extraction mixture, e.g. through a mesh and/or a screw press, to separate and independently obtain the second extract and the spent/extracted Orris root material.

As introduced above, the second extract generally comprises the phytochemical melanogenesis inhibiting agent (B), exemplified by the iridals iriflorental and iripallidal. As such, once obtained, the second extract may be used directly in the formulation of a functional composition, such as those described below for skin lightening applications, or may instead be subjected to post-extraction processing to give a final second extract composition. For example, in some embodiments, the filtrate obtained after the second extraction and post-extraction filtration is concentrated to remove all or some of the second extraction solvent therefrom and give the second extract as a concentrate. The particular concentration process is not particularly limited, and the final amount of solvent/solids in the second extract may be independently selected, e.g. based on a desired end-use thereof. For example, in certain embodiments, the second extract is concentrated to reach a final solids content in the range of from 25 to 35%, such as about 30% total solids. Of course, the final concentration of the phytochemical melanogenesis inhibiting agent (B) (e.g. iriflorental and/or iripallidal) may vary, and may be readily determined by one of skill in the art via myriad known analytical techniques, such as those illustrated in the examples herein. In certain embodiments, the second extract, in the form of the concentrate, is freeze dried and milled to obtain the second extract as a powder.

Figure 5:
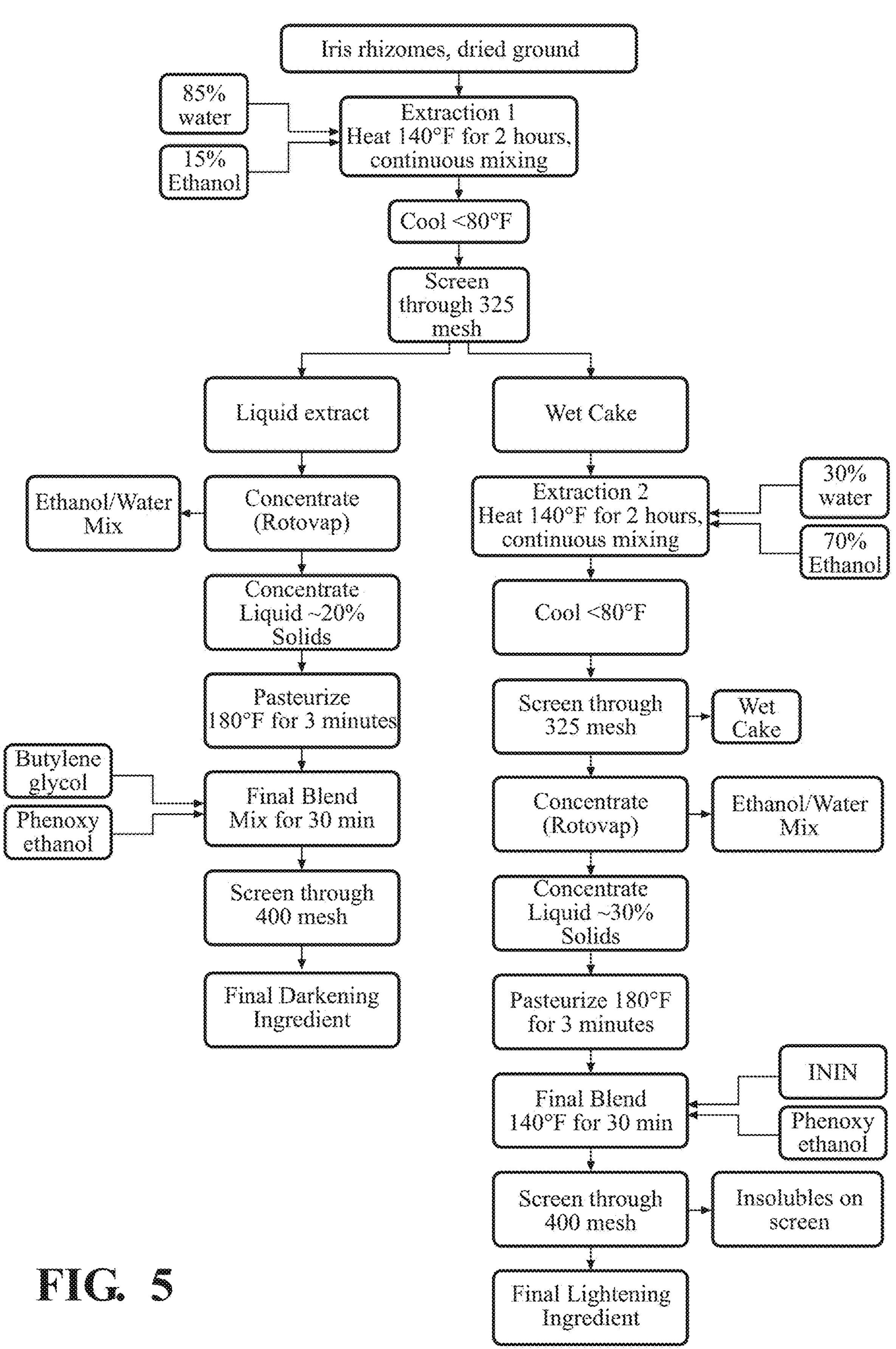
FIG. 5 shows a flow chart of one embodiment of a method of preparing an Orris root extract.

In some embodiments, the first and/or second extract and/or concentrates of the first and/or second extracts may be sterilized, e.g. via pasteurization or other heating/cooling protocol. One such embodiment is depicted in FIG. 5. In certain embodiments, the first and/or second extract is sterilized after the extract is concentrated. Similarly, additives such as carriers (e.g. isononyl isononanoate) and preservatives (e.g. phenoxyethanol) may be added to the first and/or second extracts during preparation of the same.

In general, both the first and second extracts comprise germanaism B. However, the differential extraction provided herein in the embodiments of the preparation method provides for the first extract to be enriched in germanaism B and depleted in the iridals that possess antagonistic activity. Likewise, the second extract is generally enriched in iriflorental and/or iripallidal, and depleted in germanaism B.

In certain embodiments, the first and second extracts may also comprise at least one cosmetically acceptable carrier. In specific embodiments, the cosmetically acceptable carrier is not naturally occurring. In other words, the carrier is not a product of nature in these specific embodiments. In other embodiments, the carrier is selected from conventional carriers understood in the art, and can be used in conventional amounts.

Amount of Phytochemical Melanogenesis Affecting Agents

Generally, the particular phytochemicals extracted from the Orris root material may be present in the first or second extract in any suitable concentrations, which can be selected or otherwise determined based on requirements of specific end applications. In some embodiments, for example, each extract comprises the relevant phytocompounds (e.g. phytochemical (A) or (B)) in an amount of at least 0.1%, alternatively at least 1, alternatively at least 2, alternatively at least 5, alternatively at least 10, alternatively at least 15, alternatively at least 20, alternatively at least 25, alternatively at least 30, alternatively at least 35, alternatively at least 40, alternatively at least 50, alternatively at least 55, alternatively at least 60, alternatively at least 65, alternatively at least 70, alternatively at least 75, alternatively at least 80, alternatively at least 85, alternatively at least 90, alternatively at least 95, alternatively at least 98, wt. %, based on the total weight of the extract. In some embodiments, the phytocompound fraction is selected at one of the same % values, but is compared on a w/v or v/v basis against the extract as a whole. It is to be appreciated that, in addition to the embodiments described above, the extract can be combined or otherwise supplemented with one or more additional compounds, e.g. for the purposes of enriching the composition of the extract with respect to those one or more compounds in particular.

It is to be appreciated that, while described herein in terms of the concerted two-step extraction process, the preparation method need not be utilized to obtain two finishing extracts for further use, but may instead be utilized to selectively prepare an Orris root extract with relative amounts of melanogenesis stimulating and inhibiting phytocompounds suitable for use as effective agents for altering skin pigmentation. As such, the extract prepared may be tailored based on the proportion of the phytocompounds being extracted, such that the preparation method provides improved control over the functionality of the extract(s) prepared therewith.

Functional Composition

As introduced above, a functional composition comprising the extract is also provided. More specifically, as will be appreciated from this disclosure, the functional composition may be formulated to prepare various consumer compositions (i.e., personal care products in the form of topical compositions) suitable for administration to a subject, e.g. to provide one or more components of the extracts thereto. In this context, the terms "administer," "administering," or "administration" are used herein in their broadest sense to refer to any method of delivering the functional composition, as described herein, to the subject.

The subject is typically an animal, such as a mammal (i.e., vertebrates of the class Mammalia, such as dogs, cats, goats, sheep, pigs, cattle, horses, donkeys, camels, and the like). Additional mammals that are specifically contemplated herein include semi-domesticated mammals and mammals that are routinely bred in captivity. Of course, the term mammal also encompasses humans (which may be referred to as "people" and/or "person(s)"). When describing a human, the term "adult" is typically used herein to refer to a human that has reached sexual maturity. By contrast, the terms "child" and "juvenile" are used herein to refer to a human that has not yet reached sexual maturity. Typically, the term "child" means a human subject between the stage of birth and the age of about 10 (i.e., childhood), and the term "juvenile" means a human subject that is greater than the age of about 10 and who has not completed the stage of puberty. Of course, the terms child, juvenile, adult, and infant are all encompassed by the term human, which is itself a subcategory of mammal, which is a subcategory of animal as defined herein. The subject may be a specific subset or population of the types described above. For example, in certain embodiments, the subject may be characterized as an elderly person (i.e., at least 60, alternatively at least 65, alternatively at least 70, alternatively at least 75, years of age), an athlete, a balding-male, a new mom, a student, a person with acne-prone skin, a teenager, late-teen, or pre-teen, etc. In particular embodiments, however, the subject is simply an adult seeking alteration of their skin pigmentation.

As introduced above, the functional composition is generally adapted to provide one or more components of the composition (e.g. the extract) to a subject in order to achieve a specific effect. More specifically, the component(s) of the extract may be utilized to mediate a particular therapeutic and/or prophylactic effect, such that the functional composition comprising the same may be used to treat or ameliorate a condition in the subject via melanogenesis mediation. As such, it will be understood that, in general, the functional composition comprises an effective amount of the extract (i.e., is formulated to provide a subject with an effective amount, alternatively a therapeutically effective amount of, the phytochemical melanogenesis stimulating agent (A) or the phytochemical melanogenesis inhibiting agent (B)). The term "therapeutically effective amount" as used herein refers to its meaning as is generally accepted in the art. Specifically, the term generally refers to the amount of the functional composition that will elicit the desired and/or requisite biological response in the subject (e.g. skin lightening/darkening). For example, if a given treatment/application is considered effective when there is at least about a 25% reduction in a measurable parameter associated with a disease or disorder, a therapeutically effective amount of a drug for the treatment of that disease or disorder is that amount necessary to effect at least about a 25% reduction in that parameter.

As used herein, the terms "treatment" or "treating" may be used interchangeably, and refer to an approach for obtaining beneficial or desired results including but not limited to a therapeutic benefit and/or a prophylactic benefit. A therapeutic benefit can mean eradication or amelioration of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

In general, the functional composition can be used to ameliorate conditions, such as those introduced above, by delivering the bioactive phytocompounds to the subject (i.e., to mediate, induce, or inhibit melanogenesis in the subject).

In view of the above, it will be appreciated that the functional composition may be used to ameliorate a condition affecting a subject's skin health (e.g. melanogenesis/pigmentation). More specifically, the functional composition may be formulated as a topical composition, e.g. for topical administration to a subject. As such, in certain embodiments, the functional composition is formulated based on a specific biological activity that may be achieved via topical application and/or transdermal delivery methods in particular. Typically, the functional composition is formulated to modulate human skin and/or hair pigmentation, e.g. to darken or lighten the appearance of the skin via stimulation or inhibition of melanin production.

In some embodiments, the functional composition comprises the extract in an amount of at least 0.01 to 99.9 wt. %, alternatively from 0.1 to 90 wt. %, alternatively from 0.5 to 80 wt. %, alternatively from 1 to 50 wt. %, alternatively from 1.5 to 35 wt. %, or alternatively from 2 to 20 wt. %. In specific embodiments, the functional composition comprises the extract in an amount of about 2 wt. %.

Typically, the functional composition is formulated as a topical composition (i.e., a personal care product). For example, the extract may be formulated with an acceptable carrier to prepare the topical composition. The choices of carrier will also be selected in view of a desired end-use or application of the topical composition. For example, the topical composition may be formulated as a cream, gel, powder, paste, or freely pourable liquid, e.g. depending on a desired route of application to subject/consumer. These and other embodiments will be understood in view of the description below.

The functional composition may comprise additional components aside from the Orris root extract(s). For example, the composition may comprise one or more carriers (e.g. pharmaceutically acceptable carriers, diluents, solvents, excipients, etc.), such as any of those described below or elsewhere herein. In some embodiments, however, the functional composition consists essentially of the Orris root extract, or combination of Orris root extracts set forth above. In these or other embodiments, the functional composition consists of, alternatively consists essentially of, the extract, optionally the phytocompounds obtained via the extraction, and optionally the carrier vehicle.

In certain embodiments, for example the functional composition comprises the carrier (i.e., a carrier vehicle). Suitable carrier vehicles and components can include water (e.g. purified, deionized, etc.); organic solvents such as alcohols (particularly lower alcohols readily capable of evaporating from the skin such as ethanol), glycols (such as propylene glycol, pentylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, triglycerides, sphingolipids, and waxes; protein-based materials such as collagen and gelatin; silicone-based materials (both non-volatile and volatile) such as cyclomethicone, dimethiconol, and dimethicone copolyol; hydrocarbon-based materials such as petrolatum, hydrogenated polyisobutene, and squalane; emollient esters (such as diisobutyl adipate and caprylates), thickening agents (acrylates (carbomers), acrylamides, acryl taurates, hydroxyethylcellulose, methyl cellulose, xanthan gum, etc.), and the like, as well as derivatives, modifications, and combinations thereof. Typically, the carrier vehicle is selected to dissolve or suspend the components of the composition (e.g. the extract), and thus will be selected based on the solubility of the various phytocompounds there. However, the composition may also or instead be prepared as an emulsion, suspension, slurry, etc. In specific embodiments, the carrier is not naturally occurring. In other words, the carrier is not a product of nature in these specific embodiments. In other embodiments, the carrier is selected from conventional carriers understood in the art, and can be used in conventional amounts.

Topical Composition

As introduced above, functional composition is typically formulated as a topical composition. In general, the topical composition comprises the extract (e.g. the first or second extract) and one or more other components, which may generally be selected from carriers, coactives, additives, excipients, etc. The topical composition can be generally formulated to provide the extract to a part of a subject via direct application (e.g. topically to surfaces such as skin, mucous membranes, etc.). As such, the topical composition optionally is formulated or otherwise adapted for topical administration to a mammal (e.g. a human). For example, in various embodiments, the topical composition can be formulated to be administered to the skin of a human.

In certain embodiments the topical composition comprises the extract in an amount of at least 0.001 to 20 wt. %, alternatively from 0.01 to 15 wt. %, alternatively from 0.1 to 10 wt. %, alternatively from 0.5 to 5 wt. %, alternatively from 1 to 3 wt. %, or alternatively from 1.5 to 2.5 wt. %. In some specific embodiments, the topical composition comprises the extract in an amount of about 2 wt. %.

Certain embodiments of the topical composition, which vary in terms of formulation and/or form, are described below. However, as introduced above, the topical composition is not particularly limited with regard to substance and/or form, and may comprise any number of components/ingredients in addition to the extract, such as the other active agents and/or additives described herein. Likewise, the particular additives, carriers, adjuvants, fillers, etc. present in or combined with the topical composition may also vary. In general, the components of the topical composition will be individually or collectively selected based on an intended use of the topical composition (e.g. as a skin lightening or darkening composition). Moreover, the amount of any particular component will be individually selected, e.g. based on a desired end form (e.g. cream vs. spray, etc.). As will be appreciated by those of skill in the art in view of the description and examples herein, however, the particular components will typically be selected to maximize the effectiveness of the extract, e.g. by avoiding components that will inhibit and/or prevent migration of the components thereof (e.g. the phytochemical melanogenesis affecting agents (A)/(B)) to the skin surface, and instead selecting carrier vehicles that will facilitate transport of the phytocompounds to the skin surface or through the skin, as desired.

The topical composition may comprise any form for topical application, including powders, sprays, ointments, pastes, creams, lotions, gels, solutions, and the like, as well as combinations thereof. Said differently, the physical form of the topical composition is not particularly limited. Rather, the topical composition may be formulated as a liquid, dry powder, suspension, dispersion, emulsion (e.g. oil-in-water, water-in-oil, a water-in-silicone, etc.), gel, paste, etc., and combinations thereof. As such, it will be appreciated that the topical composition may be provided in the form of a gel, a cream, an aerosol spray, a foam, a liquid, a mousse, a pomade, a powder, a solid, or an ointment. In some embodiments, the topical composition is provided as an aqueous solution, dispersion, or emulsion.

As described above, the topical composition may be utilized to ameliorate a skin condition of and/or confer a skin-related health benefit to a subject. As such, in certain embodiments, the topical composition can comprise an active agent in addition to the extract, which may provide benefits that are the same as, similar to, or different from the benefits of the extract. For example, in various embodiments, the topical composition comprises multiple active agents in addition to the extract, which can each be independently selected (e.g. based on a desired property of the active agent, such as a benefit conferred to the subject via application of the topical composition). Such active agents may include tanning agents, lightening agents, etc., as well as pharmaceuticals, nutraceuticals, anesthetics, counterirritants, chondroprotective agents, etc., which are exemplified by those listed herein.

In some embodiments, the topical composition can comprise additives selected specifically for use in formulating and/or using the topical composition, such as a pharmaceutically/medically acceptable carrier, a functional additive, a formulation additive, or combinations of such additives, e.g. selected based on a desired form of the topical composition, use of the topical composition, etc.

In some embodiments, the topical composition comprises a pharmaceutically acceptable carrier. The pharmaceutically acceptable carrier may be a non-toxic carrier, a physiologically acceptable carrier, etc. The pharmaceutically acceptable carrier may be in the form of an emulsion, a paste, a cream, a lotion, a gel, jelly, an ointment, an oil, an aerosol, a powder, a solvent, a liposome, a micelle, a peptide (e.g. albumin), a synthetic polymer (e.g. polyethylene glycol), a natural polymer (e.g., hyaluronic acid, dextran, chitosan), an n-dimensional material (e.g. where n=0, 1, 2, 3) such as, for example, a 0-dimensional nanomaterial (e.g. quantum dot, nanoparticle, etc.), a I-dimensional nanomaterial (e.g. a nanotube, a nanorod, etc.), a 2-dimensional nanomaterial (e.g. a quantum well, a film, etc.), a 3-dimensional material, such as a matrix (e.g. polymeric matrix such as polyethylene glycol (PEG)), etc. The pharmaceutically acceptable carrier may provide timed release, modulate the pharmacokinetic properties (e.g., absorption, distribution, metabolism, excretion) of the extract or phytocompounds thereof, modulate the pharmacodynamic properties (e.g., concentration at a site of action, resulting effect, etc.) of such Orris root phytocompounds, etc. For example, the pharmaceutically acceptable carrier may be an active carrier facilitates transport of germanaism B, iriflorental, and/or iripallidal across skin. Examples of such active carriers are described below. In specific embodiments, the pharmaceutically acceptable carrier is not naturally occurring. In other words, the carrier is not a product of nature in these specific embodiments. In other embodiments, the carrier is selected from conventional carriers understood in the art, and can be used in conventional amounts.

The carrier optionally can be selected to be generally compatible with the individual components of the topical composition and to enhance, or to not interfere significantly with, the application of the extract, or at least the active phytocompounds thereof, to a surface of the skin of a subject and, optionally, to enhance or not interfere with transport of other components of the topical composition to or through the skin. General examples of suitable carriers include those that promote and/or facilitate transport of various components of the topical composition through skin. Particular examples of carriers include water (e.g. deionized), oils and/or waxes (e.g. mineral oils, synthetic oils, natural oils such as jojoba oil, castor oil, etc., and waxes formed therewith), alcohols (e.g. monols, diols, and polyols such as ethanol, isopropanol, butanediol, 1,2,6-hexanetriol etc., glycols such as ethylene glycol, propylene glycol, etc.), polyoxyalkylenes and/or polyoxyalkylene esters (e.g. polyethylene glycols, polypropylene glycols, mixed polyalkylene glycols, polyethylene glycol-8 stearates, etc.), fatty acid esters (e.g. alkyl stearates, oleates, linoleates, isopropyl palmitate, etc.), organic polymers (e.g. polyacrylamides), organic solvents (e.g. dimethylsulfoxide, dimethylformamide, dimethylacetamide, methylsulfonylmethane), and the like, as well as derivatives, modifications, and combinations thereof, and any of the other carriers described herein, such as applicable vehicle and/or vehicle components described above In some embodiments, the topical composition comprises an active carrier. The active carrier is adapted to enhance the bioavailability of the active components of the topical composition (e.g. germanaism B, iriflorental, and/or iripallidal). For example, the active carrier typically assists in penetration of the active components of the topical composition through the pores of the skin. The active carrier may also possess good skin moisturizing activity, reduces emulsion particle sizes, which helps to achieve better stability of the topical composition. In some embodiments, the active carrier improves the aesthetic appeal of the topical composition. In some embodiments, the active carrier works synergistically with additives in the topical composition, such as preservatives. In some embodiments, the active carrier improves the water resistance of the topical composition, enhancing the ability of the extracts be incorporated, e.g. into a sunscreen formulation. In some embodiments, the active carrier promotes skin repair and restructure, acts as an anti-wrinkle agent, exhibits broad-spectrum antimicrobial activity, etc. In some embodiments, the active carrier possesses good solvent and solubility properties.

Non-limiting examples active carriers, as well as components useful in preparing the same, include aqueous solvents and organic solvents, for example, alcohols such as ethanol, propanediol, butylene glycol, isopropanol, glycerin, and mixtures thereof. In some embodiments, the active carrier may include pentylene glycol, ethoxydiglycol, bis-ethoxydiglycol cyclohexane 1,4-dicarboxylate, dipalmitoyl hydroxyproline, potassium palmitoyl hydrolyzed wheat protein, glyceryl stearate, cetearyl alcohol, potassium lauroyl wheat amino acids, palm glycerides, capryloyl glycine, potassium palmitoyl hydrolyzed oat protein, behenyl alcohol, palm glycerides, sodium stearoyl glutamate, sucrose palmitate, polyglyceryl-3 sorbityl linseedate, or combinations thereof. In some embodiments, the active carrier comprises pentylene glycol, ethoxydiglycol, bis-ethoxydiglycol cyclohexane 1,4-dicarboxylate, dipalmitoyl hydroxyproline, potassium palmitoyl hydrolyzed wheat protein, glyceryl stearate, cetearyl alcohol, potassium lauroyl wheat amino acids, palm glycerides, capryloyl glycine, potassium palmitoyl hydrolyzed oat protein, behenyl alcohol, palm glycerides, sodium stearoyl glutamate, sucrose palmitate, polyglyceryl-3 sorbityl linseedate, or a combination thereof. according to some embodiments, the anti-inflammatory agent may include alpha-bisabolol, allantoin, sea whip extract, *Chamomilla recutita* (*Matricaria*) extract, tocopheryl acetate, *Camellia sinensis* leaf extract, *Curcuma longa* (turmeric) root extract, *Avena sativa* (oat) kernel extract, *Magnolia officinalis* bark extract, *Vitis vinifera* (grape) seed extract, *Zingiber officinale* (ginger) root extract, dipotassium glycyrrhizinate, or a combination thereof. In some embodiments, the collagen synthesis enhancer may include methylglucoside phosphate, *Inula* crithmoide flower/leaf extract, collagen prepeptide (e.g., g-p-hyp tripeptide), madecassoside, asiaticoside, or a combination thereof. The anti-wrinkle agent may include an *Echinacea purpurea* extract, cichoric acid, resveratrol, trifluoroacetyl tripeptide-2, or a combination thereof. The keratinocyte growth factor stimulant may include a purified form (purity of at least 95%) or an enriched extract of swertiamarin.

Other general examples of carrier vehicles include water (e.g. purified, deionized, etc.); organic solvents such as alcohols, glycols (e.g. propylene glycol, pentylene glycol, butylene glycol, glycerol/glycerin, etc.), aliphatic alcohols (e.g. lanolin); mixtures of water and organic solvents (such as water and alcohol), and mixtures of organic solvents such as alcohol and glycerol (optionally also with water); lipid-based materials such as fatty acids, acylglycerols (e.g. oils, such as mineral oil, and fats of natural or synthetic origin), phosphoglycerides, triglycerides, sphingolipids, and waxes; protein-based materials such as collagen and gelatin; silicone-based materials (both non-volatile and volatile) such as cyclomethicone, dimethiconol, and dimethicone copolyol; hydrocarbon-based materials such as petrolatum, hydrogenated polyisobutene, and squalane; emollient esters (such as diisobutyl adipate and caprylates), thickening agents (acrylates (carbomers), acrylamides, acryl taurates, hydroxyethylcellulose, methyl cellulose, xanthan gum, pectin, etc.), and the like, as well as derivatives, modifications, and combinations thereof.

In particular embodiments, the topical composition can comprise a functional additive. The functional additive is not limited, and may comprise, optionally may be, any compound or composition selected to provide a functional characteristic to, or impart a function on, the topical composition. Examples of such functional additives include anti-oxidants (e.g. alkylates hydroxytoluenes, hydroxyanisoles, etc., propyl gallate, etc.), colorants, moisturizers and emollients (e.g. sunflower oil, jojoba oil, isopropyl palmitate, etc.), perfumes (e.g. natural perfumants such as rosemary oil, synthetic perfumes, etc.), cooling agents (e.g. peppermint oil), preservatives (e.g. antimicrobial and antifungal agents, such as propylene glycol, methyl paraben, propyl paraben, diazodinyl urea, etc.), and the like, as well as derivatives, modifications, and combinations thereof. While many such additives are set forth below, additional selections are illustrated in the examples herein.

For example, in certain embodiments, the topical composition can comprise a moisturizer. Examples of suitable moisturizers include hydroxy acids (e.g. lactic acid) and their salts, glycerol, propylene glycol, pentylene glycol, butylene glycol, sodium salts of pyrrolidone carbonic acid (i.e., sodium PCA), sodium hyaluronate, polyethylene glycols (PEG) (e.g. CARBOWAX PEG 200, CARBOWAX PEG 400, CARBOWAX PEG 800, etc.), and the like, as well as derivatives, modifications, and combinations thereof. In these or other embodiments, the topical composition comprises an emollient and/or a humectant. Examples of suitable emollients or humectants include cetyl palmitate, glycerol (i.e., glycerin), polypropylene glycol-15 stearyl ether (i.e., PPG-15 stearyl ether), lanolin and derivatives thereof (e.g. lanolin alcohol, etc.), cholesterol, petrolatum, isostearyl neopentanoate, octyl stearate, mineral oil, isocetyl stearate, myristyl myristate, octyl dodecanol, octyl palmitates (e.g. 2-ethylhexyl palmitate), dimethicone, phenyl trimethicone, cyclomethicone, $C_{12}$-$C_{15}$ alkyl benzoates, dimethiconol, propylene glycols, pentylene glycols, *Theobroma grandiflorum* seed butter, shea butter, ceramides (e.g. ceramide 2, ceramide 3, etc.), hydroxypropyl bispalmitamide MEA, hydroxypropyl bislauramide MEA, hydroxypropyl bisisostearamide MEA, 1,3-bis-(N-2-(hydroxyethyl) stearoylamino)-2-hydroxy propane, bis-hydroxyethyl tocopherylsuccinoylamido hydroxypropane, urea, aloe, allantoin, glycyrrhetinic acid, dicaprylate/dicaprates, and the like, as well as derivatives, modifications, and combinations thereof.

In certain embodiments, the topical composition can comprise a preservative. Examples of suitable preservatives include ureas (e.g. imidazolidinyl urea, diazolidinyl urea, etc.), phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, quaternary ammonium preservative compounds (e.g. benzalkonium chloride, benzethonium chloride, cetrimide, dequalinium chloride, cetylpyridinium chloride, etc.), mercurial preservative agents (e.g. phenylmercuric nitrate, phenylmercuric acetate, thimerosal, etc.), piroctone olamine, *Vitis vinifera* seed oil, alcoholic preservative agents (e.g. chlorobutanol, dichlorobenzyl alcohol, phenylethyl alcohol, benzyl alcohol, etc.), and the like, as well as derivatives, modifications, and combinations thereof. In these or other embodiments, the topical composition comprises an antioxidant. Examples of suitable antioxidants include ascorbic acid and esters thereof, sodium bisulfite, butylated hydroxytoluene, butylated hydroxyanisole, tocopherols (e.g. $\alpha$-tocopherol), tocopheryl acetate, sodium ascorbate/ascorbic acid, ascorbyl palmitate, ascorbyl glucoside, propyl gallate, chelating antioxidants (e.g. ethylenediaminetetraacetic acid (EDTA), disodium EDTA, etc.), citric acid, sodium citrate, and the like, as well as derivatives, modifications, and combinations thereof.

In certain embodiments, the topical composition can comprise a formulation additive. The formulation additive is not limited, and may comprise, optionally may be, any compound or composition selected to impart a physical characteristic to the topical composition. Examples of such formulation additives include emulsifiers (e.g. isoparaffins such as $C_{13}$-$C_{14}$ isoparaffin, surfactants such as laureth-7, polymers such as polyacrylamides and polyalkyleneglycols, etc.), buffers, excipients, propellants, and the like, and combinations thereof. Typically, the formulation additive is selected based on the desired form of the topical composition. For example, in some embodiments, the topical composition is formulated as an ointment, paste, cream, and/or gel, and comprises an excipient exemplified by animal and vegetable fats, oils, waxes, paraffins, starch, tragacanth, cellulose derivatives, polyethylene glycols, silicones, bentonites, silicic acid, talc, zinc oxide, and the like, as well as derivatives, modifications, and combinations thereof. In certain embodiments, the topical composition is formulated as a powder and/or spray, and comprises an excipient exemplified by lactose, talc, silicic acid, aluminum hydroxide, calcium silicates, polyamide powders, and the like, as well as derivatives, modifications, and combinations thereof. In particular embodiments, the topical composition is formulated as a spray and a propellant, such as a volatile organic compound exemplified by halogenated hydrocarbons (e.g. hydrocarbons substituted with chlorine, fluorine, or both) and low molecular weight unsubstituted hydrocarbons (e.g. butane, propane, etc.). In general, when present, the topical composition comprises the formulation additive in an amount of from 1 to 50, alternatively from 1 to 20, wt. %, based on the total weight of the topical composition.

In particular embodiments, the topical composition can comprise a lipophilic solubilizer. Some examples of lipophilic solubilizers include non-comedogenic esters, such as adipates (e.g. diisobutyl adipate), caprylates, isononanoates (e.g. isononyl neopentanoate), ethoxylated triglycerides, and the like, as well as modifications, derivatives, and combinations thereof. Other examples of lipophilic solubilizers generally include cetyl esters, polyethylene glycol cetyl esters, hydrogenated polyisobutenes, argan oil, soybean oil, chemical UV filters/boosters (e.g. octisalate, octinoxate, butyl octyl salicylate, etc.), and the like, as well as modifications, derivatives, and combinations thereof.

In some embodiments, the topical composition can comprise a free radical stabilizer. Examples of free radical stabilizers generally include lipophilic antioxidants, such as tocotrienolss, carotenoids (e.g. tocopherol, tocopherol acetate, retinyl palmitate, tetrahexydecyl ascorbate, lutein, natural oils rich in unsaturated fatty acids such as docosahexaenoic acid, etc.), and the like, as well as modifications, derivatives, and combinations thereof In certain embodiments, the topical composition can comprise a surfactant. Examples of suitable surfactants include ionic (e.g. anionic, zwitterionic, etc.) and non-ionic surfactants. Some specific examples of such surfactants include polysorbates (e.g. polyoxyethylene (20) sorbitan monolaurate (i.e., Polysorbate 20), polyoxyethylene (20) sorbitan monopalmitate (i.e., Polysorbate 40), polyoxyethylene (20) sorbitan monostearate (i.e., Polysorbate 60), polyoxyethylene (20) sorbitan monooleate (i.e., Polysorbate 80), etc.), vegetable sorbitan stearates, steareth-10 and other octadecyl polyoxyethylene ethers, sodium dodecyl sulfates (e.g. sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (e.g. sodium deoxycholate, sodium cholate, etc.), polyoxyl castor oil, nonylphenol ethoxylate, cyclodextrins, lecithin, dimethicone copolyol, lauramide diethanolamine, cocamide diethanolamine, cocamide monoethanolamine, betaines (e.g. oleyl betaine, cocamidopropyl betaine, etc.), cocamidopropyl phosphatidyl PG-dimonium chloride, dicetyl phosphate (dihexadecyl phosphate), ceteareth-10 phosphate, polyglyceryl-2 triisostearate, cetyl PEG/PPG-1/1 dimethicone (ethoxylated or organo-modified silicones for W-in-Si emulsions, glyceryl stearate, glyceryl dilaurate, lecithin, unsaturated lecithin, etc.), methylbenzethonium chloride, and the like, as well as modifications, derivatives, and combinations thereof.

In some embodiments, the topical composition can comprise an emulsifier, which may be the same as or different from the surfactant. Examples of such emulsifiers include behentrimonium methosulfate-cetearyl alcohol, non-ionic emulsifiers (e.g. emulsifying waxes), polyoxyethylene oleyl ethers, polyethylene glycol stearates (i.e., PEG-40 stearate, PEG-100 stearate, etc.), cetostearyl alcohols (e.g. cetearyl alcohol), ceteareth-12, ceteareth-20, ceteareth-30, ceteareth alcohol, glyceryl stearate, steareth-2 and steareth-20, cationic emulsifiers (e.g. stearamidopropyl dimethylamine, behentrimonium methosulfate, etc.), and the like, as well as modifications, derivatives, and combinations thereof.

In particular embodiments, the topical composition can comprise a viscosity adjusting agent (e.g. a thickening or thinning agent, which may be referred to as a viscosity modifier). Examples of such agents generally include protective colloids, non-ionic gums such as hydroxyethylcellulose, xanthan gum, and *sclerotium* gum, magnesium aluminum silicate, silica, microcrystalline waxes, beeswax, paraffin, cetyl palmitate, and the like, as well as modifications, derivatives, and combinations thereof.

In certain embodiments, the topical composition can comprise one or more additional components, which may comprise or be selected skin protectants, adsorbents, demulcents, emollients, moisturizers, hydrators, buffering agents, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g. witch hazel, alcohol, chamomile extract, etc.), binders/excipients, buffering agents, chelating agents, film forming agents, conditioning agents, opacifying agents, lipids, pH adjusters (e.g. citric acid, sodium hydroxide, sodium phosphate monobasic, sodium phosphate dibasic, etc.), and the like, as well as modifications, derivatives, and combinations thereof. Specific examples of such additional components are exemplified in U.S. Patent Application Publication No. 2018/0110722 A1, the disclosure of which regarding topical composition components is incorporated by reference herein.

In some embodiments, the topical composition comprises one or more additional components selected from thickeners, emulsion stabilizers, emulsifiers, emollients, conditioners, humectants, moisturizers, preservatives, antioxidants, pH adjusters, surfactants, fragrances, etc. In some such embodiments, the topical composition may further include at least one additional cosmetic agent, such as a vitamin, sunscreen, anti-aging agent, anti-wrinkle agent, anti-oxidant, anti-redness agent, moisturizing agent, exfoliating agent, or a combination thereof. Examples of suitable anti-oxidant additives include *Olea europaea* (olive) fruit extract, *Terminalia ferdinandiana* (*Kakadu* plum) fruit extract, soy isoflavones, and *Juglans regia* (walnut) seed extract. In some embodiments, the anti-oxidant may also act as an anti-wrinkle agent.

In these or other embodiments, the topical composition comprises the hydrator. In such embodiments, the hydrator may be selected from compounds known to penetrate the skin and absorb/retain water (e.g. sodium hyaluronate), as well as those useful for facilitating transport of water and/or hydrating compounds to or through the skin (e.g. liposomes). For example, in some embodiments, the topical composition comprises liposomes, such as those formed from or otherwise comprising omega fatty acids (e.g. omega 3, 6, and/or 9 fatty acids). Other hydrators may also be utilized, such as those known or otherwise sold under the name Acquacell, representing a blend of water, glycerin, *Citrullus* vulgaris (watermelon) fruit extract, *Pyrus* malus (apple) fruit extract, Lens *esculenta* (lentil) fruit extract, sodium pyrrolidone carboxylic acid (PCA), and sodium lactate, as well as Lubrajel (e.g. oil free), representing a blend of glycerin and glyceryl acrylate/acrylic acid copolymer and PVM/MA copolymer.

In some embodiments, the topical composition comprises the oil controller, such as zinc (PCA), a white willow bark extract, a witch hazel extract, a hexamethylene diisocyanate (HDI)/trimethylol hexyllactone crosspolymer, silica, or a combination thereof. In these or other embodiments, the topical composition comprises the exfoliant, such as an oat extract, a sugar or sugar derivative, or a combination thereof. In these or other embodiments, the topical composition comprises the anti-irritant, and wherein the anti-irritant comprises a glycyrrhizate salt, an astringent (e.g. a witch hazel extract); or a combination thereof. In these or other embodiments, the topical composition comprises one or more cosmetic additives, such as an acerola cherry extract, a biosaccharide gum, a fragrance, glycerin, butylene glycol, disodium EDTA, a polyoxyethylene ether of cetyl and/or stearyl alcohol or any combination thereof.

The topical composition can optionally include a topical moisturizer (e.g., skin protectant). Any suitable topical skin protectant can be employed, provided the skin is effectively protected or moisturized and the skin protectant remains stable in the formulation. Suitable skin protectants include, e.g. aloe, lanolin, glycerin, calamine, Vitamin E, Vitamin E acetate, Vitamin C, allantoin, aluminum hydroxide gel, bismuth subnitrate, boric acid, calamine, cocoa butter, dimethicone, glycerin, kaolin, live yeast cell derivative, petrolatum, pyridoxine hydrochloride, shark liver oil, sodium bicarbonate, sulfur, tannic acid, topical starch, trolamine, white petrolatum, zinc acetate, zinc carbonate zinc oxide, zinc sulfate, shea butter, and any combination thereof.

As used herein, calamine is a pink powder of zinc oxide and a skin protectant containing about 98% zinc oxide and about 0.5% ferric oxide; aloe is the dried latex of leaves of Curaco Aloe (Aloe barbadenis Miller, Aloe vera Linne) or Cape Aloe (Aloe *ferox* Miller and hybrids), of the family Liliacaea; Vitamin E is 3,4-dihydro-2,5,7,8-tetramethyl-2-(4,8,12-trimethyltridecyl)-2H-1-benzopy-ran-6-ol; Vitamin E acetate is 3,4-dihydro-2,5,7,8-tetramethyl-2-(4,8,12-trimethyltridecyl)-2H-1-benzopy-ran-6-ol acetate; and lanolin is the fat-like secretion of the sebaceous glands of sheep (i.e., complex mixture of esters and polyesters of 33 high molecular weight alcohols and 36 fatty acids) which is deposited onto the wool fibers. In one embodiment, the topical moisturizer can be aloe and Vitamin E.

Aloe is commercially available as Aloe Vera Gel from Terry Laboratories (Melbourne, Fla.). Aloe Vera Gel is commercially available as Aloe Vera Gel 40.times. (20.0 wt. % solution in water), Aloe Vera Gel 1.times. (0.5 wt. % solution in water), Aloe Vera Gel (5.0 wt. % solution in water), or solid Aloe Vera. The solid Aloe Vera can be dissolved in a carrier, such as water, to the desired concentration. In addition, the commercially available forms of Aloe Vera are optionally available as decolorized Aloe Vera.

Any suitable amount of topical moisturizer can be employed, provided the suitable amount of topical moisturizer or skin protectant effectively protects or moisturizes the skin and the effective amount of skin protectant remains stable in the formulation over a prolonged period of time. The suitable and effective amount of topical moisturizer can depend in part upon the specific moisturizer or moisturizers present in the formulation. In a specific embodiment, the nature and amount of the topical moisturizer is selected, such that it will be generally recognized as safe (GRAS) for topical use.

The topical composition can optionally include one or more polyhydric alcohols. Suitable polyhydric alcohols include, e.g., ethylene glycol, propylene glycol, triethylene glycol, tetraethylene glycol, sorbitol, or any combination thereof. Specifically, the polyhydric alcohol can include propylene glycol. Any suitable amount of polyhydric alcohol can be employed. For example, when present in the topical composition, the polyhydric alcohol can be present up to about 35 wt. % of the topical composition, up to about 15 wt. % of the topical composition, or up to about 5 wt. % of the topical composition. In one embodiment, the polyhydric alcohol can be present in about 0.5 wt. % to about 5.0 wt. % of the topical composition.

The topical composition can optionally include water, e.g., deionized water (DI). Any suitable amount of water can be employed, provided the amount of water maintains the adhesiveness of the adhesive and maintains the appropriate stability of the topical composition. For example, deionized water can be present up to about 50 wt. % of the topical composition, up to about 40.0 wt. % of the formulation, or up to about 30.0 wt. % of the topical composition. In one embodiment, deionized water can be present up to about 20.0 wt. % of the topical composition. In one embodiment, deionized water can be present up to about 10.0 wt. % of the topical composition. In one embodiment, deionized water can be present in about 5.0 wt. % to about 15.0 wt. % of the topical composition.

Personal Care Ingredient/Composition

In some embodiments the topical composition is formulated for use as a personal care composition, and further comprises a personal care ingredient. Examples of personal care compositions include antiperspirants and deodorants, skin care creams, skin care lotions, moisturizers, facial treatments (e.g. acne or wrinkle removers), personal and facial cleansers, bath oils, perfumes, colognes, sachets, sunscreens, pre-shave and after-shave lotions, shaving soaps and lathers, shampoos, conditioners, hair colorants, hair relaxants, hair sprays, mousses, hair gels, permanents, depilatories, cuticle coats, make-ups, color cosmetics, foundations, concealers, blushes, lipsticks, eyeliners, mascara, oil removers, color cosmetic removers, and medicament creams, pastes or sprays (e.g. for anti-acnes, dental hygienics, antibiotics, healing promotives, etc.).

The specific personal care ingredient, or a mixture of specific personal care ingredients, may be selected based on the type of personal care composition the composition is being formulated as. In these embodiments, the personal care ingredient may be a liquid, a solid, an encapsulated liquid, etc. Various examples of the personal care ingredient are described below. Any of these personal care ingredients, or a combination of two or more different personal care ingredients, may be utilized as the personal care ingredient. For clarity and consistency, "the personal care ingredient" encompasses embodiments where the composition includes but one or two or more personal care ingredients.

In specific embodiments, the personal care ingredient is an antiperspirant and/or deodorant (AP/DEO) agent. In these embodiments, the composition may be referred to as an antiperspirant and/or deodorant (AP/DEO) composition. Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllincopper complex, triclosan, aluminum zirconium octachlorohydrate, zinc ricinoleate, and mixtures thereof.

In certain embodiments, the personal care ingredient comprises a skin care ingredient. If utilized to prepare the composition, the skin care ingredient is typically selected from water phase stabilizing agents, cosmetic biocides, conditioning agents (which may be silicone, cationic, hydrophobic, etc.), emollients, moisturizers, colorants, dyes, ultraviolet (UV) absorbers, sunscreen agents, antioxidants, fragrances, antimicrobial agents, antibacterial agents, antifungal agents, antiaging actives, anti-acne agents, skin-lightening agents, pigments, preservatives, pH controlling agents, electrolytes, chelating agents, plant extracts, botanical extracts, sebum absorbents, sebum control agents, vitamins, waxes, surfactants, detergents, emulsifiers, thickeners, propellant gases, skin protectants, film forming polymers, light scattering agents, and combinations thereof. In some of these embodiments, the composition may be referred to as a skin care composition, a cosmetic composition, a sunscreen, a shower gel, a soap, a hydrogel, a cream, a lotion, a balm, foundation, lipstick, eyeliner, a cuticle coat, a blush, etc., based on the particular personal care ingredients utilized. Various species of such skin care ingredients are set forth below, with similar and alternative species known by one of ordinary skill in the art.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as $C_{30-45}$ alkyl methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched $C_8$-$C_{16}$ esters; isohexyl neopentanoate; ester oils such as isononyl isononanoate, cetostearyl octanoate, isopropyl myristate, palmitate derivatives (e.g. dextrin palmitate), stearates derivatives, diisostearyl malate, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Examples of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, $C_{30-45}$ alkyldimethylsilyl polypropylsilsesquioxane), stearyl dimethicone, alkylmethylsiloxanes including long-chain alkyl groups in alkylmethylsiloxy units, and mixtures thereof.

Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxyethylcellulose, hydroxypropylcellulose, polypropylhydroxyethylcellulose), starch and starch derivatives (such as hydroxyethylamylose and starch amylase), polyoxyethylene, carbomer, alginates (such as sodium alginate), arabic gum, cassia gum, carob gum, scleroglucan gum, gellan gum, rhamsan gum, karaya gum, carrageenan gum, guar gum and guar gum derivatives, cocamide derivatives (including cocamidopropyl betaine and cocamide MIPA), alkyl alcohols (such as cetearyl alcohol, stearyl alcohol, and other fatty alcohols), gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols such as ethyl alcohol, and hydrocolloids, and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Example of preservatives and cosmetic biocides include paraben derivatives (e.g. methylparaben, propylparaben), hydantoin derivatives, chlorhexidine and its derivatives, imidazolidinyl urea, diazolidinyl urea, phenoxyethanol, silver derivatives, salicylate derivatives, triclosan, ciclopirox olamine, hexamidine, oxyquinoline and its derivatives, PVPiodine, zinc salts and derivatives such as zinc pyrithione, methylchloroisothiazolinone, methylisothiazolinone, and mixtures thereof.

Examples of sebum absorbants or sebum control agents include silica silylate, silica dimethyl silylate, dimethicone/vinyl dimethicone crosspolymer, polymethyl methacrylate, cross-linked methylmethacrylate, aluminum starch octenylsuccinate, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc., and mixtures thereof. Surface treatments include those treatments based on lecithin, silicone, silanes, fluoro compounds, and mixtures thereof.

Examples of silicone conditioning agents include silicone oils such as dimethicone; silicone gums such as dimethiconol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats, e.g. Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between 290-320 nanometers (the UV-B region) and those which absorb ultraviolet light in the range of 320-400 nanometers (the UV-A region), as well as blue light absorbers, as known in the art.

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethylhexyl methoxycinnamate (or octyl methoxycinnamate), octyl salicylate (or ethylhexyl salicylate), oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, octyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, VA/crotonates/methacryloxybenzophenone-1 copolymer, and mixtures thereof.

Examples of skin protectants include allantoin, aluminium acetate, aluminium hydroxide, aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2-methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl) methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; *Haematoxylon brasiletto* wood extract; HC dyes; *Lawsonia inermis* (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl $C_{21}$-$C_{22}$ isoalkyl acidate; isatin; *Isatis tinctoria* leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; 1,2,4-trihydroxybenzene.

Examples of fragrances include perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-lonone, Beta-lonone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone, 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran. The fragrance may be derived or extracted from flowers, seeds, leaves, and/or roots of plants, seaweed, etc. The fragrance may be extracted from an animal, e.g. from a secretion gland, and may be a musk or sperm oil. The fragrance may also be artificially synthesized, e.g. menthol, acetate, vanilla, etc.

In specific embodiments, the perfume ketones are selected for odor character from Alpha Damascone, Delta Damascone, Iso Damascone, Carvone, Gamma-Methyl-lonone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

In specific embodiments, the perfume aldehyde is selected for odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl) oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3) (4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carbox aldehyde, 5 or 6 methoxy 10 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena I, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, phydroxyanisole, BHT, tbutyl hydroquinone, caffeic acid, *Camellia sinensis* oil, chitosan ascorbate, chitosan glycolate, chitosan salicylate, chlorogenic acids, cysteine, cysteine HCl, decyl mercaptomethylimidazole, erythorbic acid, diamylhydroquinone, ditbutylhydroquinone, dicetyl thiodipropionate, dicyclopentadiene/tbutylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxyPEG7 rutinyl succinate, methylene ditbutylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (*Melaleuca* aftemifolia) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth5, tocophereth10, tocophereth12, tocophereth18, tocophereth50, tocopherol, tocophersolan, tocopheryl linoleate, tocopheryl nicotinate, tocoquinone, otolyl biguanide, tris(nonylphenyl) phosphite, ubiquinone, zinc dibutyldithiocarbamate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

In a specific embodiment, the functional composition is a sunscreen. In these embodiments, personal care ingredient comprises the sunscreen agent. The sunscreen agent may be, for example, a sunscreen additive, an SPF booster, a photostabilizer, a film-forming polymer, etc. The sunscreen may be also or alternatively be utilized in sunless tanning applications. Specific examples of sunscreen agents are set forth above.

In other embodiments, the personal care ingredient comprises a hair care ingredient. In these embodiments, the composition may be referred to as a hair care composition. If utilized to prepare the functional composition, the hair care ingredient is typically selected from conditioning agents (which may be silicone, cationic, hydrophobic, etc.), colorants, dyes, ultraviolet (UV) absorbers, preservatives, plant extracts, fatty alcohols, vitamins, fragrance, anti-dandruff agents, color care additives, pearlising agents, pH controlling agents, electrolytes, chelating agents, styling agents, ceramides, amino-acid derivatives, suspending agents, surfactants, detergents, emulsifiers, thickeners, oxidizing agents, reducing agents, film-forming polymers, and combinations thereof. With some of these hair care embodiments, the composition may be referred to as a shampoo, a rinse-off conditioner, a leave-in conditioner, a gel, a pomade, a serum, a spray, a coloring product, or mascara. Examples of many of these hair care ingredients are set forth above as suitable personal care ingredients.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof. Examples of reducing agents are ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioproprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of antidandruff agents include pyridinethione salts, selenium compounds such as selenium disulfide, and soluble antidandruff agents, and mixtures thereof.

In certain embodiments, the personal care ingredient comprises a film-forming polymer, which may be utilized as the personal care ingredient whether the functional composition is utilized for skin care, hair care, etc. "Film-forming polymer," as used herein, means a polymer or oligomer which is capable of, by itself or optionally in the presence of a film-forming agent, forming a film on a substrate. The film-forming polymer may form the film upon an application of a curing condition, e.g. the application of heat, exposure to atmospheric conditions, etc. Alternatively, the film-forming polymer may form the film upon evaporation of any carrier vehicle in which the film-forming polymer may optionally be disposed. The film-forming polymer may undergo a reaction, e.g. the film-forming polymer may become cross-linked or otherwise include additional bonds, when forming the film. However, the film-forming polymer may form the film in the absence of such a reaction. The film-forming polymer may be a gelling agent. The film-forming polymer is particularly advantageous when the functional composition is formulated as a sunscreen, although the personal care ingredient may comprise the film-forming polymer in other forms of functional composition as well.

Personal Care Active

In various embodiments, the personal care ingredient may comprise or be referred to as a personal care active, a health care active, or combination thereof (collectively "active" or "actives"). As used herein, a "personal care active" means any compound or mixtures of compounds that are known in the art as additives in personal care formulations, typically for providing a cosmetic and/or aesthetic benefit. A "healthcare active" means any compound or mixtures of compounds that are known in the art to provide a pharmaceutical or medical benefit. Thus, "healthcare active" includes materials considered as an active ingredient or active drug ingredient as generally used and defined by the United States Department of Health & Human Services Food and Drug Administration, contained in Title 21, Chapter I, of the Code of Federal Regulations, Parts 200-299 and Parts 300-499. Specific personal care actives and health care actives are described below. These personal care actives and health care actives may constitute the personal care ingredient whether the personal care ingredient is utilized to form, for example, the AP/DEO composition, the skin care composition, the hair care composition, the nail care composition, and/or the tooth care composition. For example, in various embodiments, the same personal care ingredient may be utilized to form either the hair care composition or the skin care composition. As understood in the art, at least some of the personal care actives described below are species of certain personal care ingredients introduced above with respect to the skin care composition, the hair care composition, the nail care composition, and the tooth care composition, respectively. For example, numerous species of plant or vegetable extracts are described below, which are exemplary examples of plant extracts set forth above as suitable personal care ingredients. The active ingredients or actives described below may constitute the personal care ingredient of the topical composition or may be utilized in combination therewith.

Useful personal care active ingredients for use in the topical composition include vitamins and vitamin derivatives, including "pro-vitamins". Vitamins useful herein include, but are not limited to, Vitamin A1, retinol and its derivatives (e.g. $C_2$-$C_{18}$ esters of retinol, trans-retinol, 1,3-cis-retinol, 11-cis-retinol, 9-cis-retinol, and 3,4-didehydro-retinol, as well as trans retinoic acids (i.e., retinoids)), Vitamin B1, Vitamin B2, Pro Vitamin B5, panthenol, Vitamin B6, Vitamin B12, niacin, Vitamin C and its derivatives, vitamin E, tocopherol, esters of vitamin E, folic acid, biotin, pantothenic acid, and mixtures thereof. Other suitable vitamins and the International Nomenclature Cosmetic Ingredient (INCI) names for the vitamins suitable for use in the topical composition include ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate, retinyl acetate, retinyl palmitate, retinyl propionate, α-tocopherol, tocophersolan, tocopheryl acetate, tocopheryl linoleate, tocopheryl nicotinate, and tocopheryl succinate, as well as combinations thereof.

The personal care active can be a protein, such as an enzyme. Enzymes include commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include proteases (bacterial, fungal, acid, neutral or alkaline), amylases (alpha or beta), lipases, mannanases, cellulases, collagenases, lisozymes, superoxide dismutase, catalase, and mixtures thereof. Proteases include trypsin, chymotrypsin, pepsin, pancreatin and other mammalian enzymes; papain, bromelain and other botanical enzymes; subtilisin, epidermin, nisin, naringinase (L-rhammnosidase) urokinase and other bacterial enzymes. Lipase include triacyl-glycerol lipases, monoacyl-glycerol lipases, lipoprotein lipases, e.g. steapsin, erepsin, pepsin, other mammalian, botanical, bacterial lipases and purified ones.

Co-Actives

Examples of other active agents suitable for use in the topical composition are described below. One or more of these active agents can be used, either alone or in combination with the actives and/or additives described herein.

The topical composition may include an antiparasite agent. Examples of antiparasitic agents include hexachlorobenzene, carbamate, naturally occurring pyrethroids, permethrin, allethrin, malathion, piperonyl butoxide, and combinations thereof.

The topical composition may include an antimicrobial agent, also referred to as germicidal agents. Examples of antimicrobial agents include phenols, including cresols and resorcinols. Such compositions may be used to treat infections of the skin. An example of a very common skin infection is acne, which involve infestation of the sebaceous gland with p. *acnes*, as well as *Staphylococus aurus* or *Pseudomonas*. Examples of useful antiacne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g. cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate and cholate; parachlorometaxylenol; and combinations thereof.

Phenols, in concentrations of 0.2, 1.0, and 1.3, % by weight, are generally bacteriostatic, bactericidal, and fungicidal, respectively. Several phenol derivatives are more potent than phenol itself, and the most important among these are the halogenated phenols and bis-phenols, the alkyl-substituted phenols and the resorcinols. Hydrophobic antibacterials include triclosan, triclocarbon, eucalyptol, menthol, methylsalicylate, thymol, and combinations thereof.

The topical composition may include an antifungal agent. Examples of antifungal agents include azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and combinations thereof. U.S. Pat. No. 4,352,808 discloses 3-aralkyloxy-2, 3-dihydro-2-(1H-imidazolylmethyl)benzo[b]thiophene compounds having antifungal and antibacterial activity, which are incorporated herein by reference.

The topical composition may include a steroidal anti-inflammatory agent. Examples of steroidal anti-inflammatory agents include corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafal, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and combinations thereof.

Topical antihistaminic preparations currently available include 1 percent and 2 percent diphenhydramine (Benadryl® and Caladryl®), 5 percent doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines can also be included in the composition. Additionally, "natural" anti-inflammatory agents may be useful. For example, candelilla wax, alpha bisabolol, aloe vera, Manjistha (extracted from plants in the genus *Rubia*, particularly *Rubia cordifolia*), and Guggal (extracted from plants in the genus *Commiphora*, particularly *Commiphora mukul*, may be used as an active in the topical composition.

The topical composition may include a non-steroidal anti-inflammatory drug (NSAID). Examples of NSAIDs include the following NSAID categories: propionic to acid derivatives; acetic acid derivatives; fenamic acid derivatives; biphenylcarboxylic acid derivatives; and oxicams. Such NSAIDs are described in the U.S. Pat. No. 4,985,459, which is incorporated herein by reference. Further examples include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen, bucloxic acid, and combinations thereof.

The topical composition may include an antioxidant/radical scavenger. Examples of antioxidants include ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, the ascorbyl esters of fatty acids, amines (e.g. N,N-diethylhydroxylamine, amino-guanidine), sulfhydryl compounds (e.g. glutathione), and dihydroxy fumaric acid and its salts may be used, as well as EDTA, BHT and the like, and combinations thereof.

The topical composition may include an antibiotic. Examples of antibiotics include chloramphenicol, tetracyclines, synthetic and semi-synthesic penicillins, beta-lactames, quinolones, fluoroquinolnes, macrolide antibiotics, peptide antibiotics, cyclosporines, erythromycin, clindamycin, and combinations thereof.

The topical composition may include a topical anesthetic. Examples of topical anesthetics include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, pharmaceutically acceptable salts thereof, and combinations thereof.

The topical composition may include an anti-viral agent. Examples of anti-viral agents include certain proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell. In particular, anti-viral agents include nucleoside analogs (e.g. zidovudine, acyclovir, acyclovir prodrugs, famciclovir, gangcyclovir, vidarabine, idoxuridine, trifluridine, and ribavirin), n-docosanoll foscarnet, amantadine, rimantadine, saquinavir, indinavir, ritonavir, idoxuridine alpha-interferons and other interferons, AZT, and combinations thereof.

Additional examples of actives include analgesic agents and antihypertensive agents. Analgesic agents are known in the art and are colloquially referred to as painkillers. The analgesic agent may be selected from any known analgesic agents, and specific examples thereof include paracetamol (acetaminophen), morphine, codeine, heroine, methadone, thebaine, orpiarine, buprenorphine, morphinans, benzomorphans, acetaminophen, butorphanol, diflunisal, fenoprofen, fentanyl, fentanyl citrate, hydrocodone, aspirin, sodium salicylate, ibuprofen, oxymorphone, pentaxicine, naproxen, nalbuphine, mefenamic acid, meperidine and dihydroergotamine, non-steroidal anti-inflammatory agents, such as salicylates, and opioid agents, such as morphine and oxycodone. Antihypertensive agents are known in the art for treating or reducing hypertension, i.e., high blood pressure.

The antihypertensive agent may be selected from any known antihypertensive agents, and specific examples thereof include diuretics, adrenergic receptor antagonists (e.g. beta blockers), benzodiazepines, calcium channel blockers, renin inhibitors, etc.

A typical narcotic antagonist is haloxone. Exemplary antitussive agents include diphenhydramine, guaifenesin, hydromorphone, ephedrine, phenylpropanolamine, theophylline, codeine, noscapine, levopropoxyphene, carbetapentane, chlorpehndianol and benzonatate.

Exemplary sedatives include chloral hydrate, butabarbital, alprazolam, amobarbital, chlordiazepoxide, diazepam, mephobarbital, secobarbital, diphenhydramine, ethinamate, flurazepam, halazepam, haloperidol, prochlorperazine, oxazepam, and talbutal.

Examples of cardiac drugs include quinidine, propranolol, nifedipine, procaine, dobutamine, digitoxin, phenyloin, sodium nitroprusside, nitroglycerin, verapamil HCl, digoxin, nicardipine HCl, and isosorbide dinitrate.

Antiemetics are illustrated thiethylperazine, metoclopramide, cyclizine, meclizine, prochlorperazine, doxylamine succinate, promethazine, triflupromazine, and hydroxyzine.

A typical dopamine receptor agonist is bromocriptine mesylate. Exemplary amino acid, peptide and protein hormones include thyroxine, growth hormone (GH), interstitial cell stimulating hormone (ICSH), follicle-stimulating hormone (FSH), thyrotropic hormone (TSH), adrenocorticotropic hormone (ACTH), gonadotropin releasing hormone (GnRH) such as leuprolide acetate, vasopressin and their active degradation products Some products may have sufficiently high molecular weights that absorption through the stratum corneum or mucous membranes may be difficult. Therefore, in some embodiments, the only hormones having molecular weights and stereo configurations allowing passage through the skin are utilized. Example of hormones include estradiol, diethylstilbestrol, conjugated estrogens, estrone, norethindrone, medroxyprogesterone, progesterone, norgestrel, testosterone, methyltestosterone, and fluoxymesterone.

In particular embodiments, the topical composition comprises a combination of the extract and the additional active agent. In such embodiments, the functional composition may be homogeneous or mixed as a unitary composition or, alternatively, may be adapted as a kit including a first component comprising the extract and a second component comprising the additional active agent. The components of the kit may be administered together or separately (e.g. sequentially, in any order).

Additive Component

In addition to the components described above (i.e., the composition/extract, the pharmaceutically acceptable additive, etc.), the topical composition may comprise any number of additional ingredients/components. For example, in some embodiments, the topical composition comprises an additive component, which may comprise one or more additives.

Examples of suitable additives for use in the additive component include amino acids, peptides, proteins, lipids, vitamins, carbohydrates, nucleic acids, minerals, nutrients, antioxidants, probiotic bacterial strains, lipotropic agents, extracts, concentrates, oils, gums, and combinations thereof. In certain embodiments, the additive component comprises a flavoring agent, a dye, a flow modifier, a preservative, a filler, a binder, a dispersing agent, a solubilizer, a supplemental nutrient, an excipient, a buffer, a lubricant, a sweetener, a wetting agent, or any combination thereof. Particular examples of suitable additives include vitamin A, vitamin D, calcium, methyl cellulose, lecithin, lysolecithin, and long-chain fatty alcohols. In particular embodiments, the additive component comprises a carrier, such as a consumable, nutritional, and/or pharmaceutical carrier, or a combination thereof.

In certain embodiments, the additive component of the topical composition comprises one or more of the following: excipients, such as diluents and binders; granulating agents; glidants (or flow aids); fillers; lubricants; stabilizers; bulking agents; anti-caking agents; coatings; disintegrants; fragrances; natural or artificial sweeteners; flavorings; and pigments; alcohols, such as ethanol, propyl alcohol and benzyl alcohol; glycerin; glyceryl triacetate; mineral oils; water; silicones, such as silicone oils; silicon dioxide; waxes, such as carnauba wax and beeswax; fatty esters and fatty alcohols; carob; corn syrups, such as hydrolyzed corn syrup solids; cellulose, such as methyl cellulose, hydroxypropyl methyl cellulose, carboxy methyl cellulose, microcrystalline cellulose, and powdered cellulose; fructose; maltodextrin and maltol, such as natural maltol; sorbitol; preservatives, such as p-hydrobenzoic acid esters; potassium sorbate; sodium benzoate; flow agents; stearates, such as calcium stearate, magnesium stearate, and sodium magnesium stearate; dicalcium phosphate; vegetable oils, such as hydrogenated vegetable oils; antioxidants, such as ascorbic acid or tocopherol; starches, such as corn starch and potato starch; glycols and polyglycols; moisturizers; emollients; emulsifiers; surfactants; oils; extracts; skin protectants; disinfectants; antiseptics; drugs and drug substances; analgesic compounds; anti-neuralgic compound; anti-oxidants; blood circulation promoters; antidepressant compounds; anti-anxiety compounds; anti-stress compounds; colorants; fillers; solvents; vehicles; carriers; other types of additives known to those of skill in the art; and combinations thereof.

It is to be appreciated that each additive may be utilized in the topical composition in any amount, which is typically selected based on the type of additive, the formulation of the topical composition, a desired end use of the topical composition, etc. It is also to be appreciated that certain additives may be classified under different terms of art, and may have similar, overlapping, or different functions with additives having different classifications. In certain embodiments, each additive is present in the functional composition in an amount of from greater than 0 to 75 wt. %, based on the total mass of the composition, such as in an amount of 1, 2, 3, 4, 5, 10, 15, 20, 25, 30, 35, 40, 45, 50, 55, 60, 65, 70, or 75, wt. %, based on the total mass of the composition, or in an amount in a range bounded by any two of such values.

The topical composition may be presented in a unit dosage form, such as in a pack (e.g. metal or plastic foil, blister pack, etc.) or dispenser device including one or more unit doses of the composition. The pack or dispenser device may be accompanied by instructions for administration. Useful dosage forms can be prepared by methods and techniques that will be well understood by those of skill in the art and may include the use of additional ingredients in producing bulk or dosage forms, such as those described below. Although exemplary dosages, dose frequencies, and methods of administration are discussed herein, these are merely exemplary and it is to be understood that the dose, dose frequency, and mode of administration may vary according to the age, body weight, condition and response of the individual subject, consumer, or patient, and the particular formulation of the topical composition.

As will be understood in view of the description below, the topical composition, in any form, may be administered as needed, daily, several times per day or in any suitable regimen such that a desired outcome is achieved. In a treatment method utilizing the topical composition, the frequency of administration can depend on several factors, including a desired level of prevention or amelioration. Generally, an exemplary regimen includes administration of the topical composition to the subject once or twice daily, e.g. including an administration in the morning and/or an administration in the evening. The amount of the topical composition administered to the subject during each administration (i.e., the dose) may depend on several factors, such as the level of results desired, and the specific topical composition being utilized, the number of doses being administered, etc.

In general, the topical composition is administered in a therapeutically or physiologically effective amount, which, as introduced above, relates to an amount (i.e., a quantity) of a composition (e.g. the topical composition of the present embodiments) required to achieve a particular therapeutic and/or prophylactic effect, such as in treating a subject (e.g. by ameliorating a condition thereof). Likewise, as used herein, the term "physiologically effective amount" relates to an amount of a composition (e.g. the topical composition of the present embodiments) required to achieve a desired physiological effect. Such effective amounts are typically measured and/or expressed in terms of the amount of the topical composition over time (e.g. g/day, mg/day, etc.), but may also incorporate the body weight of the subject (e.g. in kg), as expressed by the unit g/kg/day. Typically, the topical composition is administered in an amount effective to provide the extract (i.e., the phytocompounds thereof) to the subject. In certain embodiments, the topical composition is administered in an amount effective to ameliorate a condition of the subject. In these or other embodiments, the functional composition is administered in an amount effective to ameliorate at least two conditions of the subject, including any of those described herein.

Active Amount/Concentration

The topical composition, in any of the forms described herein, may comprise any amount of the extract, which will typically be limited by nature of the particular phytocompound content (e.g. germanaism B or iriflorental and/or iripallidal) therein. Specifically, daily exposure limits are specified by numerous regulatory/governing organizations, and are being regularly investigated and updated based on the increasing understanding of biological effects of such compounds. As such, particular amounts and limits of any given phytocompound present in the topical composition may vary, even irrespective of potency (i.e., where a more-potent content is prohibited by law or rule).

In addition to the forms of the topical composition described above, it will be appreciated that the composition may be formulated into for dermal (or trans-dermal) delivery/administration to a subject. In such embodiments, the topical composition may be prepared in a form for use in, on, with, and/or as an ointment, patch (i.e., a transdermal patch), intradermal implant, subcutaneous implant, or transdermal implant. As used herein, "dermal delivery" or "dermal administration" refers to a route of administration wherein the pharmaceutical dosage form is taken to, or through, the dermis (i.e., layer of skin between the epidermis (with which it makes up the cutis) and subcutaneous tissues). The transdermal patch is typically provided as a medicated adhesive patch that is placed on the skin to deliver a specific dose of the phytochemical melanogenesis stimulating or inhibiting agent (A/B) through the skin and into the bloodstream of a subject. Such patches are known in the art, and may be utilized with the functional composition generally to provide a therapeutic route of administration to subjects.

The various forms of the topical composition will be best understood in view of the exemplary compositions below. Such compositions may be tailored for specific application and/or dosage regimens, which will be readily understood by those of skill in the art.

The personal care composition can be used by any method, such as via application to a human body (e.g. skin or hair) by hand or with an applicator (e.g. a brush or sprayer). In some embodiments, the personal care composition may be intended to be removed after such application, e.g. by washing, wiping, peeling, and the like, or combinations thereof.

A method of ameliorating (e.g. treating, preventing) a condition with the topical composition (the "treatment method") is also provided. The treatment method comprises administering the topical composition to a subject in an amount effective to elicit a biological response from the subject. In certain embodiments, the treatment method comprises administering the topical composition topically to the subject, e.g. in the form of the personal care product.

EXAMPLES

The following examples, illustrating embodiments of this disclosure, are intended to illustrate and not to limit the invention. Unless otherwise noted, all reactions are carried out under air, and all solvents, substrates, and reagents are purchased or otherwise obtained from various commercial suppliers and utilized as received. All components are mixed or blended according to conventional combination routes.

Iris Plant Growth

Authentication: *Iris florentina* L. specimens were obtained from a commercial nursery (Companion Plants, Athens, Ohio) and grown in Grant County, Washington State using organic farming practices.

Verification of plant morphology characteristics was made using benchmarks provided by the American Iris Society to help authenticate specimens as *Iris florentina* L. HPTLC phytochemical profiles of extracts obtained from several specimens were also examined by an authenticating laboratory (Alkemist Labs, Costa Mesa, CA) and found to be consistent with the profile of *Iris germanica*.

Further testing using a universal plant DNA test (DNA Species Identification SOP AT-SP-278-7, NSF Authentechnologies, Petaluma, CA) confirmed that specimens were consistent with *Iris florentina* and *Iris germanica*.

Because the phytochemical profiles and DNA tests did not conclusively differentiate *Iris florentina* from *Iris germanica* varieties, a further comparative investigation using whole genome sequencing was conducted. Chloroplast DNA sequences were used to locate single nucleotide polymorphisms (SNPs) for several different *Iris germanica* cultivars and *Iris florentina* specimens. Twenty-one positions were initially identified in an algorithmic search, and eleven were confirmed by observation. Primers were developed for five of these sequences and used for DNA testing. Of these, three SNPs successfully differentiated *Iris florentina* specimens from other *Iris germanica* varieties tested.

Washing Process For Rhizomes:

Rhizomes were dug out of the field with hairy roots and soil still attached. Rhizomes and roots were washed in 5-gal buckets using potable water from the Columbia River supplied by the Irrigation District in Ephrata, WA. After washing, the hairy roots were removed using hand clippers. The rhizome was hand sliced in 2-5 millimeter slices using a kitchen knife until as much rhizome was removed from the plant.

Process Ranges Tested For Solvent Extraction:

Extraction Solvent Ranges: Various extraction conditions were evaluated, and assessed on the basis of extraction yield.

First extractions were tested across the range of 0-30% ethanol in water. With 0% EtOH (100% water) very little germanaism was extracted with the first extract, and also resulted in lower irifloreintal in the second extract. With 30% ethanol in first extract (70% water), high amounts of germanaism B were extracted in the first extract, but iriflorental was reduced in the second extract. A first extraction using 15:85 EtOH/$H_2O$ was determined best for a skin-lightening extract. A first extraction using 30:70 EtOH/$H_2O$ was determined best for a skin darkening extract. The best balance was determined to also be the 15:85 EtOH/$H_2O$ solvent system, which removed measurable amount of germanaism B in the first extract, while giving the maximum concentration of iriflorental in the second extract.

Second extractions were tested across the range of 70-84% ethanol in water. All extractions provided similar results, thus 70% (i.e., 70:30 EtOH/$H_2O$) was chosen for economy.

Mix time of second extract+ININ: tested 20, 40, and 60 minutes with similar results on marker levels. 30 minutes was selected as a mid-point for further analysis.

Extraction time, temperature, and feedstock/solvent ratio: Times from 60-120 minutes, temperatures from 100-140° F., and feedstock:solvent ratios from 1:8 to 1:10 were evaluated.

Slightly more material was extracted during the 120 minutes at the 1:10 ratio, and these parameters were selected for further work. Notably, as temperature was reduced, the yield from the extraction went down, thus 140° F. was utilized.

Adding a water wash on the feedstock in between the first and second extracts (Method #3 in Table 1 below) will reduce the concentration of germanaism and increase the concentration of iriflorental, with a down side of reduced yield on the second extract (the lightening ingredient). Method #1 provided a good balance of effective lightening with favorable yields.

The first extraction removes very little iriflorental, but has similar concentration of Germ B. See Row 3 in Table 1 below. This shows it helps to reduce Germ B concentration in the second extract, allowing for lightening activity in second extract and darkening activity in the first extract.

TABLE 1

Marker Levels On First And Second Extract, In Different Processes

| Germ. B (mg/g as Daidzin) | Iriflorental (mg/g as 10-gingerol) | Method | Form | Description |
|---|---|---|---|---|
| 62.86 | 5.474 | 2 | Freeze Dried Powder | Second Extract, no water wash. |
| 19.88 | 10.554 | 3 | Freeze Dried Powder | Second extract, with water wash. Measurable improvement on markers, but extraction yield significantly reduced |
| 64.42 | 0.338 | 2 | Freeze Dried Powder | First Extract (darkening enriched). Much lower concentration of iriflorental and similar concentration of germ. B |

Variations on the extraction methods utilized to prepare the extracts are illustrated in the flow diagrams of FIGS. 5-7.

Process Ranges Tested For Supercritical Fluid Extraction (SCFE) With $CO_2$:

Temp was always 55° C., tested range of 80-200 bar, extraction time of 15-60 minutes, with and without 20% ethanol as a co-solvent, packed column vs unpacked.

The best results (based on 3d tissue model) were obtained with an unpacked column with either 200 bar for 60 minutes and $CO_2$ only, or an unpacked column with 20% ethanol cosolvent and 100-200 bar. By using ethanol as a cosolvent with the $CO_2$, similar results were obtained at lower pressures.

The SCFE-based method utilized to prepare extracts is illustrated in the flow diagrams of FIG. 8.

LC and LCMS

Reagents: Water, acetonitrile, and isopropanol were Optima LC-MS grade from Fisher Scientific. Formic Acid was LC-MS grade from Sigma-Aldrich. Mobile phase solvents were prepared as 0.1% formic acid solutions in water (Solvent A) or acetonitrile (solvent B). DMSO was HPLC grade from Fisher Scientific. Germanaism B and iriflorental reference standards were isolated from extracts of *Iris florentina* L. rhizome by the Center for Natural Products Research, University of Mississippi, with structural confirmation by 1H and 13C NMR, and high resolution mass spectrometry.

Instrumentation: Liquid chromatography-mass spectrometry (LC-MS) analyses and bioassay directed fractionation (BDF) were performed using a Waters Synapt G2 instrument equipped with an Acquity H-class UPLC. Effluent from column was directed to a Photodiode Array Detector (PDA), and subsequently to the electrospray (ES) ionization source of the mass spectrometer. UV data was acquired from 200-800 nm at 1.2 nm resolution at a sampling rate of 5 scans/sec. Mass spectral data was collected in both positive and negative ion modes at 20,000 resolving power (FWHM) from m/z 50-1200 at 0.25 scans/s. Within each run, alternating low energy (4V) and high energy (20V) collision induced dissociation scans were collected, using argon as collision gas (MSe mode). Leucine-enkephalin was used as the lock mass for accurate mass analysis.

LC-MS analysis. Sample extracts were prepared at 10 mg/mL in DMSO, and sonicated for 20 min to solubilize. Process samples were diluted 1:10 in isopropanol. All samples were filtered through a 0.2 μm Whatman Anotop 25 syringe filter into autosampler vials for assay. The column was a Waters Acquity HSS T3, 1.8 μm, 2.1×100 mm and the column oven was maintained at 40° C. The solvent program was ramped linearly as follows: 90% A/10% B at time 0, to 100% B at 6 min, hold at 100% B to 8 min, then to 90% A/10% B at 8.01 min, and hold at 90% A/10% B to 10 min. A flow rate of 0.4 mL/min and an injection volume of 2 μL were used. Tentative identification of compounds was made based of the accurate mass determined for the protonated (or deprotonated) molecule and by comparison to on-line mass spectral databases. Compounds identified are shown in Table 2 below.

TABLE 2

| Table of Compounds | | | | | | | |
|---|---|---|---|---|---|---|---|
| Peak No. | Compound | CAS No | $t_R$ (min) | Formula | Measured [M + H]+ | Calc. | Error (ppm) |
| 1 | Irisolone 4'-O-diglucoside | 50938-05-1 | 3.36 | $C_{29}H_{32}O_{16}$ | 637.1769 | 637.1763 | 0.9 |
| 2 | Iridin | 491-74-7 | 3.49 | $C_{24}H_{26}O_{13}$ | 523.1449 | 523.1452 | −0.6 |
| 3 | Germanaism B | 123648-56-6 | 3.65 | $C_{23}H_{22}O_{11}$ | 475.1237 | 475.1240 | −0.6 |
| 4 | Germanaism A | 471271-89-3 | 3.69 | $C_{24}H_{24}O_{12}$ | 505.1343 | 505.1346 | −0.6 |
| 5 | Irilone 4'-O-glucoside | 50868-47-8 | 3.95 | $C_{22}H_{20}O_{11}$ | 461.1073 | 461.1084 | −2.4 |
| 6 | Irisolidone 7-O-glucoside | 126308-74-5 | 4.11 | $C_{23}H_{24}O_{11}$ | 477.1398 | 477.1397 | 0.2 |
| 7 | Irigenin | 548-76-5 | 4.57 | $C_{18}H_{16}O_8$ | 361.0914 | 361.0923 | −2.5 |
| 8 | Irisolidone | 2345-17-7 | 5.4 | $C_{17}H_{14}O_6$ | 315.0868 | 315.0869 | −0.3 |
| 9 | Iriflorental | 86293-26-7 | 7.52 | $C_{31}H_{50}O_4$ | 487.3780 | 487.3787 | −1.4 |
| 10 | Iripallidal | 86293-27-8 | 7.68 | $C_{31}H_{50}O_4$ | 487.3779 | 487.3787 | −1.6 |

Bioassay Directed Fractionation (BDF)

Sample extracts were prepared at 50 mg/ml in DMSO and sonicated for 20 min. Samples solutions were then filtered through 0.2 μm Whatman Anotop 25 syringe filter into autosampler vials for assay. The LC-MS system was modified to incorporate a 10:1 splitter that was positioned between the UV detector and MS ion source. The majority of LC effluent was directed to a Waters Fraction Collector II fitted with a 96-deep well plate into which fractions were collected by time at intervals of 20 sec/well for the first 32 minutes of each run (96 wells/run). The LC column was a XBridge Shield RP18, 5 μm, 4.6×250 mm maintained at ambient temperature (22° C.). The solvent program was ramped linearly as follows: 95% A/5% B at time 0, to 100% B at 30 min, hold at 100% B to 32 min, then to 95% A/5% B at 32.1 min and hold 95% A/5% B until 36 min. The flow rate was 0.8 mL/min and an injection volume of 10 L/injection was used (0.5 mg solids/injection). Effluent from four consecutive LC runs was collected per plate (2 mg solids/plate). Plates were then dried under nitrogen at 40° C. to remove acetonitrile and residual water was removed by freeze drying. Plates were stored at −80° C. until to assayed for pigmentation response.

The results of the BDF are shown in FIG. 2, with LC-UV chromatogram A at 260 nm showing phytochemical peak profile, and time-aligned bar graph B (with each bar representing a fraction from the LC effluent collected for 20 seconds), showing pigmentation responses using B16 cell culture assay. Increased pigmentation is observed for the fraction corresponding to germanaism B (3) and reduced pigmentation is observed for fractions corresponding to iriflorental (9) and iripallidal (10).

Cell Culture

Primary cells and cell lines were grown in a humidified atmosphere of 5% $CO_2$ at 37° C. B16-F10 (B16) cells obtained from ATCC (Manassas, VA, USA) were cultured in Dulbecco's Modified Eagle's Medium with 4.5 g/L glucose, L-glutamine, sodium pyruvate (DMEM) supplemented with 10% fetal bovine serum (FBS) and 1% P/S Solution, 100×. The cells were sub-cultured in T75 flasks three to four days each not exceeding 70% confluency to sustain regular growth. Experiments were performed between the fourth and sixth passages.

Human Epidermal Melanocytes, neonatal, darkly pigmented (HEMn-DP) cells were procured from Thermo Fisher Scientific (Waltham, MA, USA) and maintained in Medium 254 with 60 UM calcium and supplemented 1% Human Melanocyte Growth Supplement (Thermo Fisher Scientific) and 1% Penicillin-Streptomycin (P/S) Solution, 100× (Corning, Manassas, VA, USA). Cells were cultured in T75 and T150 flasks and passaged before 80% confluency. Experiments were performed between the fourth and sixth passages.

B16 Melanin Content Assay

B16 cells (6000 cells/well) were pre-cultured in 96-well plates in DMEM medium supplemented with 10% FBS and 1% P/S for 24 hours. For treatments, cells were treated with the vehicle or the testing articles in 0.2 ml DMEM-phenol free medium supplemented with 10% FBS, 1% P/S, 2 mM L-glutamine, and 50 nM α-MSH (Sigma, St. Louis, MO, USA) for 96 hours. The absorbance at 405 nm was measured, and MTT (3-(4,5-dimethylthiazol-2-yl)-2,5-diphenyltetrazolium bromide) assay was performed to examine the viability of cells. Relative melanin content was normalized with the % cell viability.

HEMn-DP Melanin Content Assay

HEMn-DP cells (300,000 cells/well) were pre-cultured in a 6-well plate in a growth medium. After 24 hours of incubation, the cells were treated with a vehicle control and the testing articles on Day 1 and 4. On Day 7, the growth medium was removed, and the cells were lysed using a lysed buffer (Thermo Fisher Scientific). The lysed cells were centrifuged at 10,000 g for 10 minutes, and the pellet was washed with ethanol:ether (1:1) solution. The pellets were dried, then solubilized in 2N of NaOH at 80° C. for 1 hour. The extracts were transferred to a 96-well plate, and the total melanin content was measured with M5 Spectramax plate reader at 405 nm. The cell viability was determined using PrestoBlue (Thermo Fisher Scientific) following a manufacturer's protocol.

Figure 3:
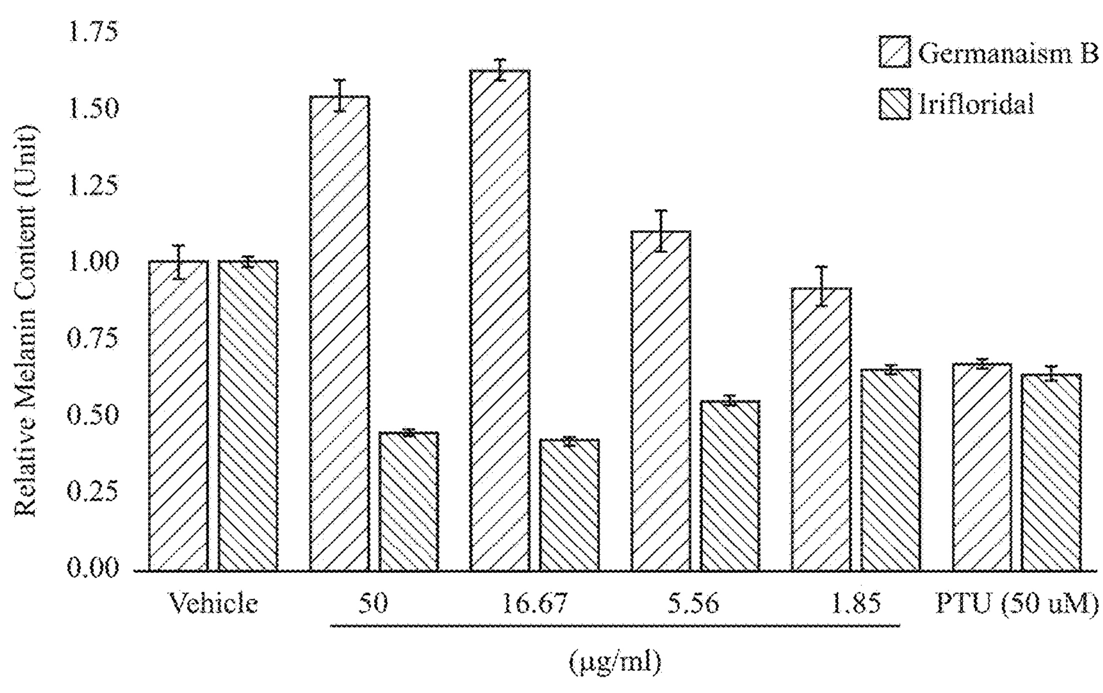
FIG. 3 provides the results of a B16 pigmentation assay, showing the effect of purified germanaism b and irifloridal on melanin production.

The results of the assay are shown in FIG. 3, where PTU is propylthiouracil, a standard melanogenesis inhibitor.

Human Skin Equivalent Maintenance and Treatment

The MelanoDerm™ skin equivalents (Mattek Corp, Ashland, MA) derived from African-American skin (MEL-B) were placed in an incubator containing 5% $CO_2$ at 37° C. The tissues were maintained in the LLMM medium. The testing articles were dissolved in vehicle control solution (90% PBS+5% EtOH+5% Propylene glycol) at desired concentrations. After 3 hours of incubation, 25 μL of the vehicle control and the testing articles were applied topically to the skin equivalents on Days 0, 1, 3, 6, 8, 10, and 13. The tissues were washed with PBS between the treatments and replenished with 5 ml of fresh media every other day. On day 14, the tissues were collected for the visual analysis, melanin extraction and a cytotoxicity assay.

Human Skin Equivalent Cell Viability Assay

A vehicle control and testing articles (25 μl) were applied topically to MEL-B on Days 0, 1, 3, 6, 8, 10, and 13. Untreated samples were used as negative controls. On Day 14, tissues were rinsed with PBS and placed in 24 well plates. A 2 mg/ml solution of MTT was prepared, and 0.3 ml of the solution was added to the wells. After 3 hours of incubation, the tissues were transferred to the 6-well plate containing 3.0 ml of isopropanol. The plates were stored in −20° C. overnight, then shaken for at least two hours at room temperature. The extract solution was measured at 570 nm.

Human Skin Equivalent Melanin Content Assay

Melanin content in treated MEL-B was determined as previously reported. Briefly, the frozen tissues were immersed in 0.38 ml of 1% SDS, 50 UM EDTA, and 10 mM Tris, pH 6.8, and 20 μl of protease K was added at 5 mg/ml. Digestion proceeded overnight at 45° C., and an additional 20 μl of protease K was added for an additional 4 hours of incubation. Then, 40 μl of 500 mM sodium carbonate and 10 μl of 30% H2O2 were added to the homogenates. The samples were incubated at 80° C. for 30 min and cooled to room temperature. Chloroform/methanol (2:1) mixture was prepared and 100 μl was added to the samples. After centrifugation at 10,000 g for 30 min, top phases were collected, and the optical density was measured at 450 nm. Synthetic melanin (Sigma-Aldrich) was subjected to the same procedure as a control, and a standard curve was constructed.

Figure 4:
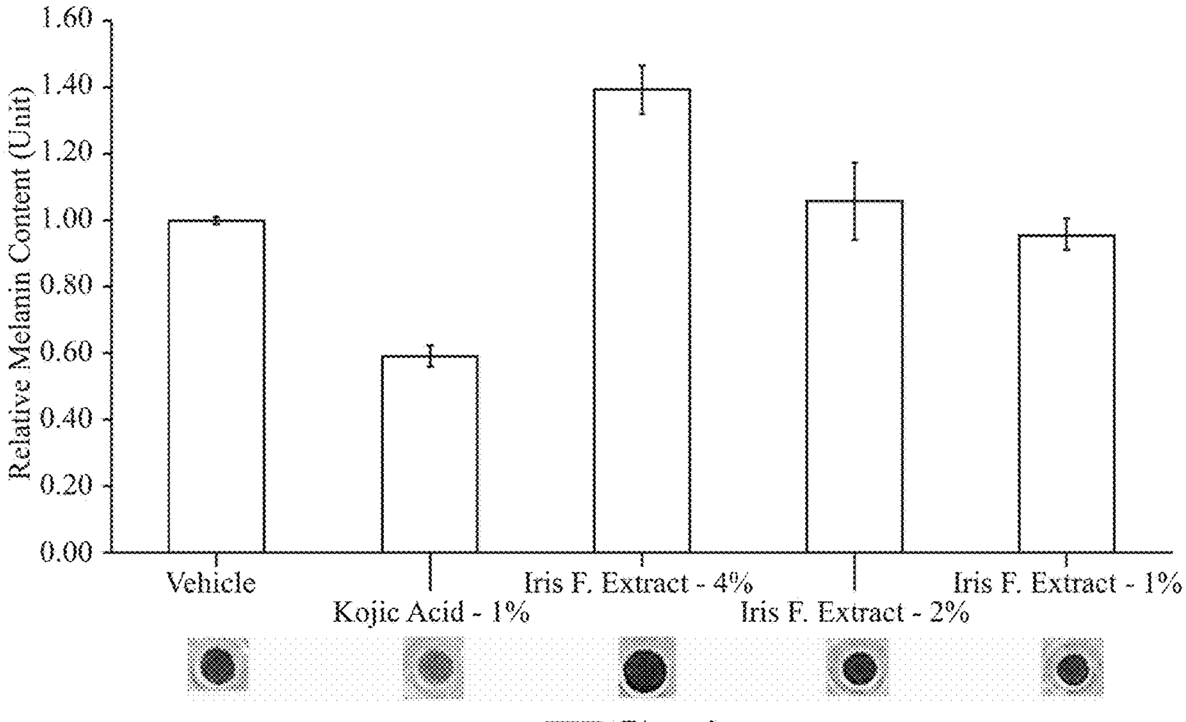
FIG. 4 provides the results of a skin equivalent tissue melanoderm assay, showing the effect of a selective Orris root extract on melanin production.

The results of the Assay are shown in FIG. 4.

Serum Compositions

A series of serum formulas for tissue model testing are prepared as shown in Table 3 below.

TABLE 3

Lecithin Serum Formulas for 3D Tissue Model Testing

| Raw Material Description | Vehicle Control % | Iris Root Extract % | Iris ISO OP (Silab) % | Ascorbyl Glucoside % | Kojic Acid % |
|---|---|---|---|---|---|
| Water, Purified | 88.200 | 84.200 | 85.100 | 87.700 | 87.950 |
| Hydrogenated Lecithin | 2.000 | 2.000 | 2.000 | 2.000 | 2.000 |
| Caprylic/Capric Triglyceride | 2.000 | 2.000 | 2.000 | 2.000 | 2.000 |
| Xanthan Gum | 0.300 | 0.300 | 0.300 | 0.300 | 0.300 |
| Sodium Citrate | 0.500 | 0.500 | 0.500 | 0.500 | 0.500 |
| Glyceryl Stearate | 1.000 | 1.000 | 1.000 | 1.000 | 1.000 |
| Cetyl Alcohol | 1.000 | 1.000 | 1.000 | 1.000 | 1.000 |
| Behenyl Alcohol | 1.000 | 1.000 | 1.000 | 1.000 | 1.000 |
| Isononyl Isononanoate | 4.000 | 4.000 | 4.000 | 4.000 | 4.000 |
| Sodium Hydroxide (50% Solution) | — | — | 0.100 | 0.500 | 0.250 |
| 96% Isononyl Isononanoate (and) 4% Iris Florentina Root Extract solids | — | 4.000 | — | — | — |
| 90% Butylene Glycol (and) 7.20% Water (and) 2.80% Iris Florentina Root Extract | — | — | 3.000 | — | — |
| Ascorbyl Glucoside | — | — | — | 2.000 | — |
| Kojic Acid | — | — | — | — | 2.000 |
| TOTAL | 100.000 | 100.000 | 100.000 | 100.000 | 100.000 |
| pH= | 6.96 | 6.94 | 6.85 | 6.56 | 6.65 |
| Viscosity= | 3900 cP | 5000 cP | Not recorded | Not recorded | Not recorded |

Personal Care Products

Various examples of topical compositions, formulated as personal care products, are provided below.

Skin Lightening

Formulation Example 1: Facial Foam Cleanser. A personal care product composition in the form of a Facial Foam Cleanser for skin lightening is prepared using the components and parameters shown Table 4 below.

TABLE 4

Components of Formulation Example 1: Facial Foam Cleanser

| Raw Material Description | % |
|---|---|
| Water, Purified | 48.4750 |
| Butylene Glycol | 0.5000 |
| Disodium EDTA | 0.0500 |
| Glycerin | 2.5000 |
| Xanthan Gum | 0.1500 |
| Butylene Glycol (and) Glycerin (and) Chlorphenesin (and) Methylparaben | 3.4000 |
| Dipotassium Glychrrhizinate | 0.0200 |
| Panthenol | 0.1000 |
| Polysorbate 20 | 0.3000 |
| Polyacrylate 13 (and) Polyisobutene (and) Polysorbate 20 | 1.0000 |
| Cetearyl Alcohol (and) Cetearyl Glucoside | 1.0000 |
| Mineral Oil | 12.0000 |
| Isododecane | 3.0000 |
| Meadowfoam Seed Oil | 2.0000 |
| *Butyrospermum Parkii* (Shea) Butter | 3.0000 |
| Dimethicone | 2.0000 |
| Glyceryl Trioctanoate | 5.0000 |
| Isodecyl Neopentanoate | 2.0000 |
| Tetrahexyldecyl ascorbate | 0.0500 |
| Tocopheryl Acetate | 0.1000 |
| C12-15 Alkyl Benzoate | 2.0000 |
| Caprylic/Capric Triglyceride | 6.0000 |
| Ascorbyl Glucoside | 0.1000 |
| Phenylethyl Resorcinol | 0.1000 |
| Niacinamide | 1.0000 |
| Water (and) Butylene Glycol (and) Glycerin (and) *Avena Sativa* (Oat) Kernel Extract | 1.0000 |
| Liposome w/Acerola Cherry Ferment & Licorice | 0.5000 |
| Sodium Hyaluronate | 0.0025 |
| Sodium Hyaluronate (Low Molecular Weight) | 0.0025 |
| 90% Isononyl Isononanoate (and) 5% Water (and) 4% Iris Florentina Root Extract solids (and) 1% Phenoxyethanol | 2.0000 |
| *Bellis Perennis* (Daisy) Flower Extract | 0.5000 |
| *Oenothera Biennis* (Evening Primrose) Seed Extract | 0.0500 |
| Fragrance RTA-003511 Sheer Glow M1 | 0.1000 |
| TOTAL | 100.0000 |
| pH= | 4.0-6.0 |
| Viscosity= | 29,000-50,000 cP |
| LVT, T Bar-E @ 6.0 rpm, 60 seconds (Initial) | |
| Specific Gravity= | 0.950-0.980 |

Formulation Example 2: Facial Softening Lotion/Toner. A personal care product composition in the form of a Facial Softening Lotion/Toner for skin lightening is prepared using the components and parameters shown Table 5 below.

TABLE 5

Components of Formulation Example 2: Facial Softening Lotion/Toner

| Raw Material Description | % |
|---|---|
| Water, Purified | 84.440 |
| Disodium EDTA | 0.050 |
| Dipotassium Glychrrhizinate | 0.030 |
| PEG-75 | 2.000 |
| Dipropylene Glycol | 1.500 |
| Betaine | 1.000 |

TABLE 5-continued

| Components of Formulation Example 2: Facial Softening Lotion/Toner | |
|---|---|
| Raw Material Description | % |
| Trehalose | 1.000 |
| Ascorbyl Glucoside | 2.000 |
| Phenylethyl Resorcinol | 0.500 |
| Niacinamide | 1.000 |
| Sodium Citrate Dihydrate | 0.200 |
| Potassium Hydroxide (45% Solution) | 0.740 |
| Sodium Hyaluronate | 0.050 |
| 90% Isononyl Isononanoate (and) 5% Water (and) 4% Iris Florentina Root Extract solids (and) 1% Phenoxyethanol | 2.000 |
| *Bellis Perennis* (Daisy) Flower Extract | 0.500 |
| *Oenothera Biennis* (Evening Primrose) Seed Extract | 0.050 |
| Liposome w/Ceramide 3 & Sitosterol (QD Application) | 0.100 |
| Liposome w/Acerola Cherry Ferment & Licorice | 0.010 |
| Butylene Glycol (and) Glycerin (and) Methylparaben (and) Chlorphenesin | 2.500 |

TABLE 5-continued

| Components of Formulation Example 2: Facial Softening Lotion/Toner | |
|---|---|
| Raw Material Description | % |
| Isoceteth-20 | 0.300 |
| Fragrance RTA-003511 Sheer Glow M1 | 0.030 |
| TOTAL | 100.000 |
| pH= | 6.0-7.0 |
| Viscosity= | Water thin |
| Specific Gravity= | 1.010-1.038 |

Formulation Example 3; Facial Complexion Serum Concentrate. A personal care product composition in the form of a Facial Complexion Serum Concentrate for skin lightening is prepared using the components and parameters shown Table 6 below.

TABLE 6

| Components of Formulation Example 3: Facial Complexion Serum Concentrate | |
|---|---|
| Raw Material Description | % |
| Water, Purified | 68.625 |
| Acrylates/C10-30 Alkyl Acrylate Crosspolymer | 0.100 |
| Butylene Glycol | 7.000 |
| Hydroxyethylcellulose | 0.200 |
| Xanthan Gum | 0.200 |
| Disodium EDTA | 0.100 |
| Dipotassium Glycyrrhizate | 0.030 |
| Phenoxyethanol (and) Methylparaben (and) Propylparaben (and) Ethylparaben | 0.900 |
| Glyceryl Trioctanoate | 5.000 |
| Octyl Palmitate | 2.000 |
| Dimethicone 1.5 cst | 0.500 |
| Dimethicone 5 cst | 1.250 |
| Polyglyceryl - 10 Pentastearate (and) Behenyl Alcohol (and) Sodium Stearoyl Lactylate | 2.000 |
| Batyl Alcohol | 0.500 |
| Nylon-12 | 0.500 |
| Mica (and) Titanium Dioxide (and) Triethoxycaprylylsilane | 1.500 |
| Polyglyceryl-10 Laurate (and) Dimethicone (and) Glycerin (and) Water | 1.000 |
| Ascorbyl Glucoside | 2.000 |
| Phenylethyl Resorcinol | 0.500 |
| Niacinamide | 1.000 |
| Sodium Citrate Dihydrate | 0.200 |
| Potassium Hydroxide (45% Solution) | 0.875 |
| Bisabolol (and) Zingiber Officinale (Ginger) Root Extract | 0.200 |
| Sodium Hyaluronate | 0.050 |
| 90% Isononyl Isononanoate (and) 5% Water (and) 4% Iris Florentina Root Extract solids (and) 1% Phenoxyethanol | 2.000 |
| Bellis Perennis (Daisy) Flower Extract | 0.500 |
| Oenothera Biennis (Evening Primrose) Seed Extract | 0.050 |
| Liposome w/Ceramide 3 & Sitosterol (QD Application) | 0.500 |
| Liposome w/Acerola Cherry Ferment & Licorice | 0.500 |
| Fragrance RTA-003511 Sheer Glow M1 | 0.220 |
| TOTAL | 100.000 |
| pH = | 6.2-6.8 |
| Viscosity = | 3,000-5,400 cP |
| LVT Spindle #3 @ 12 rpm for 60 seconds | |
| Specific Gravity = | 0.990-1.023 |

Formulation Example 4: Facial Spot Essence Concentrate. A personal care product composition in the form of a Facial Spot Essence Concentrate for skin lightening is prepared using the components and parameters shown Table 7 below.

TABLE 7

| Components of Formulation Example 4: Facial Spot Essence Concentrate | |
|---|---|
| Raw Material Description | % |
| Water, Purified | 36.600 |
| Butylene Glycol | 10.000 |
| Disodium EDTA | 0.050 |
| Dipotassium Glycyrrhizate | 0.200 |
| Ammonium Acryloyldimethyl Taurate/VP Copolymer | 1.000 |
| Dimethicone (and) Cyclomethicone (and) Polysilicone-11 (and) Isohexadecane (and) Ammonium Polyacryloyldimethyl Taurate (and) Polysorbate 20 (and) Polysorbate 80 (and) Tocopheryl Acetate | 30.000 |
| Isododecane | 10.000 |
| Ascorbyl Glucoside | 2.000 |
| Phenylethyl Resorcinol | 0.500 |
| Niacinamide | 1.000 |
| Sodium Citrate Dihydrate | 0.150 |
| Potassium Hydroxide (45% Solution) | 0.750 |
| 90% Isononyl Isononanoate (and) 5% Water (and) 4% Iris Florentina Root Extract solids (and) 1% Phenoxyethanol | 2.000 |
| Bellis Perennis (Daisy) Flower Extract | 0.500 |
| Oenothera Biennis (Evening Primrose) Seed Extract | 0.050 |
| Liposome w/Acerola Cherry Ferment & Licorice | 1.000 |
| Liposome w/Ceramide 3 & Sitosterol (QD Application) | 1.000 |
| Butylene Glycol (and) Glycerin (and) Chlorphenesin (and) Methylparaben | 3.000 |
| Fragrance RTA-003511 Sheer Glow M1 | 0.200 |
| TOTAL | 100.000 |
| pH = | 6.0-7.0 |
| Viscosity = LVT Spindle #3 @ 12 rpm for 60 seconds | 3,500-7,500 cP |
| Specific Gravity = | 0.955-0.975 |

Formulation Example 5: Facial Spot Corrector Treatment. A personal care product composition in the form of a Facial Spot Corrector Treatment for skin lightening is prepared using the components and parameters shown Table 8 below.

TABLE 8

| Components of Formulation Example 5: Facial Spot Corrector Treatment | |
|---|---|
| Raw Material Description | % |
| Water, Purified | 37.050 |
| Butylene Glycol | 10.000 |
| Ethoxydiglycol | 1.000 |
| Xanthan Gum | 0.400 |
| Citric Acid | 0.100 |
| Sodium Citrate Dihydrate | 0.900 |
| Disodium EDTA | 0.050 |
| Sodium Benzoate | 0.450 |
| 90% Isononyl Isononanoate (and) 5% Water (and) 4% Iris Florentina Root Extract solids (and) 1% Phenoxyethanol | 2.000 |
| Bellis Perennis (Daisy) Flower Extract | 0.500 |
| Oenothera Biennis (Evening Primrose) Seed Extract | 0.500 |
| Dipotassium Glychrrhizinate | 0.200 |
| Ascorbyl Glucoside | 2.000 |
| Phenylethyl Resorcinol | 0.500 |
| Niacinamide | 1.000 |
| Sodium Hydroxide (50% solution) | 0.550 |
| Liposome w/Acerola Cherry Ferment & Licorice | 2.000 |
| Water (and) Butylene Glycol (and) Avena Sativa (Oat) Kernel Extract | 2.000 |
| Tetrahexyldecyl Ascorbate | 0.250 |
| Cetyl PEG/PPG-10/1 Dimethicone | 3.000 |
| Cyclopentasiloxane (and) Dimethicone/Vinyl Dimethicone Crosspolymer | 34.000 |

TABLE 8-continued

| Components of Formulation Example 5: Facial Spot Corrector Treatment | |
|---|---|
| Raw Material Description | % |
| Titanium Dioxide (and) Silica (and) Triethoxycaprylylsilane | 0.750 |
| Phenoxyethanol | 0.600 |
| Fragrance RTA-003511 Sheer Glow M1 | 0.200 |
| TOTAL | 100.000 |
| pH = | NA |
| Viscosity = | 100,000-800,000 cP |
| LVT T Bar-F, @ 1.5 rpm for 60 seconds | |
| Specific Gravity = | 0.970-1.040 |

Formulation Example 6: Facial Milky Emulsion/Moisturizer, A personal care product composition in the form of a Facial Milky Emulsion/Moisturizer for skin lightening is prepared using the components and parameters shown Table 9 below.

TABLE 9

| Components of Formulation Example 6: Facial Milky Emulsion/Moisturizer | |
|---|---|
| Raw Material Description | % |
| Water, Purified | 61.408 |
| Acrylates/C10-30 Alkyl Acrylate Crosspolymer | 0.210 |
| Disodium EDTA | 0.100 |
| Dipotassium Glychrrhizinate | 0.050 |
| Glycerin | 3.000 |
| Glycereth-26 | 2.000 |
| Hydrogenated Lecithin | 0.500 |
| Squalane | 4.000 |
| Dimethicone | 0.500 |
| Caprylic/Capric Triglycerides | 4.000 |
| Isodecyl Neopentanoate | 4.000 |
| Glyceryl Stearate (and) PEG-100 Stearate | 3.000 |
| Cetyl Alcohol | 0.300 |
| Sorbitan Stearate | 1.000 |
| Sodium Hyaluronate | 0.005 |
| Sodium Hyaluronate (Low Molecular Weight) | 0.003 |
| Cyclopentasiloxane (and) Dimethiconol (and) Water (and) Laureth-4 (and) Laureth-23 | 5.000 |
| Ascorbyl Glucoside | 0.100 |
| Phenylethyl Resorcinol | 0.500 |
| Niacinamide | 1.000 |
| Potassium Hydroxide (45% solution) | 0.285 |
| Biosaccharide Gum-1 | 1.000 |
| 90% Isononyl Isononanoate (and) 5% Water (and) 4% Iris Florentina Root Extract solids (and) 1% Phenoxyethanol | 2.000 |
| Bellis Perennis (Daisy) Flower Extract | 0.500 |
| Oenothera Biennis (Evening Primrose) Seed Extract | 0.050 |
| Liposome w/Ceramide 3 & Sitosterol (QD Application) | 1.000 |
| Liposome w/Acerola Cherry Ferment & Licorice | 0.500 |
| Butylene Glycol (and) Glycerin (and) Methylparaben (and) Chlorphenesin | 3.750 |
| Fragrance RTA-003511 Sheer Glow M1 | 0.240 |
| TOTAL | 100.000 |
| pH = | 5.5-7.3 |
| Viscosity = | 60,00-25,000 cP |
| LVT Spindle #4 @ 12 rpm for 60 seconds | |
| Specific Gravity = | 0.992-1.012 |

Formulation Example 7: Facial Moisture Cream. A personal care product composition in the form of a Facial Moisture Cream for skin lightening is prepared using the components and parameters shown Table 10 below.

TABLE 10

| Components of Formulation Example 7: Facial Moisture Cream | |
|---|---|
| Raw Material Description | % |
| Water, Purified | 52.792 |
| Acrylates/C10-30 Alkyl Acrylate Crosspolymer | 0.200 |
| Disodium EDTA | 0.100 |
| Dipotassium Glychrrhizinate | 0.050 |
| Glycerin | 5.470 |
| Butylene Glycol | 1.470 |
| Hydrogenated Polyisobutane | 7.000 |
| Butyrospermum Parkii (Shea) Butter | 3.000 |
| Octyldodecanol | 2.000 |
| Glyceryl Stearate (and) PEG-100 Stearate | 3.000 |
| Cetyl Alcohol | 0.500 |
| Stearyl Alcohol | 1.500 |
| PEG-25 Stearate | 2.500 |
| C30-45 Alkyl Dimethicone | 2.500 |
| Dimethicone | 1.000 |
| Dimethicone | 6.000 |
| Ascorbyl Glucoside | 0.100 |
| Phenylethyl Resorcinol | 0.500 |
| Niacinamide | 1.000 |
| Potassium Hydroxide (45% solution) | 0.270 |
| Butylene Glycol (and) Glycerin (and) Chlorphenesin (and) Methylparaben | 3.750 |
| Sodium Hyaluronate | 0.005 |
| Sodium Hyaluronate (Low Molecular Weight) | 0.003 |
| 90% Isononyl Isononanoate (and) 5% Water (and) 4% Iris Florentina Root Extract solids (and) 1% Phenoxyethanol | 2.000 |
| Bellis Perennis (Daisy) Flower Extract | 0.500 |
| Oenothera Biennis (Evening Primrose) Seed Extract | 0.050 |
| Liposome w/Ceramide 3 & Sitosterol (QD Application) | 1.000 |
| Liposome w/Acerola Cherry Ferment & Licorice | 0.500 |
| Fragrance RTA-003511 Sheer Glow M1 | 0.240 |
| PEG/PPG/Polybutylene Glycol-8/5/3 Glycerin | 1.000 |
| TOTAL | 100.000 |
| pH = | 6.0-7.0 |
| Viscosity = | 200,000-500,000 cP |
| LVT T Bar-F @ 1.5 rpm for 60 seconds | |
| Specific Gravity = | 0.967-1.019 |

Skin Darkening

Formulation Example 8: Sunless Tanning Spray. A personal care product composition in the form of a Sunless Tanning Spray for skin darkening is prepared using the components and parameters shown Table 11 below.

TABLE 11

| Components of Formulation Example 8: Sunless Tanning Spray | |
|---|---|
| Raw Material Description | % |
| Water, Purified | 85.030 |
| Disodium EDTA | 0.100 |
| Dipotassium Glychrrhizinate | 0.030 |
| Glycerin | 0.300 |
| Hydrolyzed Jojoba Esters (and) Water | 0.500 |
| Caprylyl/Capryl Glucoside | 2.000 |
| Dipropylene Glycol | 1.500 |
| Betaine | 1.000 |
| Trehalose | 1.000 |
| Dihydroxyacetone (and) Sodium Metabisulfite (and) Magnesium Stearate | 4.000 |
| Sodium Hyaluronate | 0.005 |
| Sodium Hyaluronate (Low Molecular Weight) | 0.005 |

TABLE 11-continued

| Components of Formulation Example 8: Sunless Tanning Spray | |
|---|---|
| Raw Material Description | % |
| 90% Butylene Glycol (and) 5% Water (and) 4% Iris Florentina Root Extract solids (and) 1% Phenoxyethanol | 2.000 |
| Phenoxyethanol (and) Ethylhexylglycerin | 1.000 |
| Erythrulose (and) Water | 1.500 |
| Fragrance RTA-003511 Sheer Glow M1 | 0.030 |
| Lactic Acid (and) Water (15% Solution) | q.s. |
| TOTAL | 100.000 |
| pH = | 3.5-4.0 |
| Viscosity = | Water thin |
| Specific Gravity = | 1.010-1.038 |

Formulation Example 9: Two-Phase Self-Tanning Mousse. A personal care product composition in the form of a Two-Phase Self-Tanning Mousse for skin darkening is prepared using the components and parameters shown Table 12 below.

TABLE 12

| Components of Formulation Example 9: Two-Phase Self-Tanning Mousse | |
|---|---|
| Raw Material Description | % |
| Dicapryl Succinate | 6.000 |
| Meadowfoam (Limnanthes Alba) Seed Oil and Butyrospermum Parkii (Shea Butter) Extract | 0.500 |
| Macadamia Ternifolia Nut Oil | 0.500 |
| Helianthus Annuus (Sunflower) Seed Oil (and) Zea Mays (Corn) Oil (and) Sesamum Indicum (Sesame) Seed Oil (and) Macadamia Integrifolia Seed Oil (and) Olea Europaea (Olive) Fruit Oil | 1.000 |
| Tocopheryl Acetate | 0.500 |
| Water, Purified | 76.540 |
| Disodium EDTA | 0.050 |
| Dipotassium Glycyrrhizate | 0.200 |
| Dihydroxyacetone (and) Sodium Metabisulfite (and) Magnesium Stearate | 4.000 |
| Cocamidopropyl PG-Dimonium Chloride | 1.000 |
| Cocamidopropyl Betaine | 1.000 |
| Polyester-11 | 0.500 |
| Glycerin | 3.000 |
| Sodium Hyaluronate | 0.005 |
| Sodium Hyaluronate (Low Molecular Weight) | 0.005 |

TABLE 12-continued

| Components of Formulation Example 9: Two-Phase Self-Tanning Mousse | |
|---|---|
| Raw Material Description | % |
| Caprylhydroxamic Acid (and) 1,2-Hexanediol (and) Butylene Glycol | 1.500 |
| 90% Butylene Glycol (and) 5% Water (and) 4% Iris Florentina Root Extract solids (and) 1% Phenoxyethanol | 2.000 |
| Erythrulose (and) Water | 1.500 |
| Fragrance RTA-003511 Sheer Glow M1 | 0.200 |
| Citric Acid | q.s. |
| TOTAL | 100.000 |
| pH = | 3.5-4.0 |
| Viscosity = | Water thin |
| LVT Spindle #3 @ 12 rpm for 60 seconds | |
| Specific Gravity = | 1.010-1.038 |

Formulation Example 10: Sunless Tanning Milky Emulsion. A personal care product composition in the form of a Sunless Tanning Milky Emulsion for skin darkening is prepared using the components and parameters shown Table 13 below.

TABLE 13

| Components of Formulation Example 10: Sunless Tanning Milky Emulsion | |
|---|---|
| Raw Material Description | % |
| Water, Purified | 39.760 |
| Glycerin | 5.000 |
| Disodium EDTA | 0.200 |
| Dipotassium Glycyrrhizate | 0.030 |
| Pentylene Glycol | 5.000 |
| Polyurethane-62 (and) Trideceth-6 | 1.000 |
| Xanthan Gum | 0.300 |
| Tocopheryl Acetate | 0.200 |
| Isopropyl Isostearate | 14.000 |
| Diisostearyl Dimer Dilinoleate | 10.000 |
| Isohexadecane | 5.000 |
| PEG-20 Methyl Glucose Sesquistearate | 0.270 |
| Methyl Glucose Sesquistearate | 0.220 |
| Lactic Acid 90% Solution | 0.110 |
| Dihydroxyacetone (and) Sodium Metabisulfite (and) Magnesium Stearate | 4.000 |
| Glycerin (and) Water (and) Dextran (and) Acetyl Hexapeptide-1 | 0.500 |
| Dimethyl Isosorbide | 2.000 |
| Hydrolyzed Jojoba Esters (and) Water | 1.000 |
| Phenoxyethanol (and) Ethylhexylglycerin | 1.000 |
| Bisabolol (and) Zingiber Officinale (Ginger) Root Extract | 0.200 |
| Sodium Hyaluronate | 0.005 |
| Sodium Hyaluronate (Low Molecular Weight) | 0.005 |
| 90% Butylene Glycol (and) 5% Water (and) 4% Iris Florentina Root Extract solids (and) 1% Phenoxyethanol | 2.000 |
| Liposome w/Ceramide 3 & Sitosterol | 0.500 |
| Liposome w/Five Natural Oils & Tetrahexyldecyl ascorbate | 0.500 |
| Vitex Agnus Castus Extract & Acetyl Tyrosin & Glycerin & Alcohol & Water | 4.000 |
| Erythrulose (and) Water | 3.000 |
| Fragrance RTA-003511 Sheer Glow M1 | 0.200 |
| Citric Acid (25% Solution) | q.s. |
| TOTAL | 100.000 |
| pH = | 3.5-4.5 |
| Viscosity = | 7,000-11,000 cP |
| RVT Spindle #5 @ 20 rpm for 60 seconds | |

Formulation Example 11: Sunless Self-Tanning Lotion. A personal care product composition in the form of a Sunless Self-Tanning Lotion for skin darkening is prepared using the components and parameters shown Table 14 below.

TABLE 14

| Components of Formulation Example 11: Sunless Self-Tanning Lotion | |
|---|---|
| Raw Material Description | % |
| Water, Purified | 67.010 |
| Disodium EDTA | 0.100 |
| Dipotassium Glycyrrhizate | 0.030 |
| Glycerin | 3.000 |
| Butylene Glycol | 3.000 |
| Xanthan Gum | 0.150 |
| Caprylic/Capric Triglycerides | 6.000 |
| Tocopheryl Acetate | 0.200 |
| Butyrospermum Parkii (Shea) Butter | 1.500 |
| Tribehenin PEG-20 Esters | 2.000 |
| Glyceryl Stearate (and) PEG-100 Stearate | 1.000 |
| Dimethicone, 100 cst | 1.000 |
| Isosorbide Dicaprylate | 2.000 |
| Cetyl Alcohol | 1.000 |
| Hydroxyethylacrylate (and) Sodium Acryloyldimethyl Taurate Copolymer (and) Squalane (and) Polysorbate 60 | 1.000 |
| Hydrolyzed Jojoba Esters (and) Water | 1.000 |
| Dihydroxyacetone (and) Sodium Metabisulfite (and) Magnesium Stearate | 4.000 |
| Citric Acid (25% Solution) | 0.100 |
| Phenoxyethanol (and) Ethylhexylglycerin | 1.000 |
| Bisabolol (and) Zingiber Officinale (Ginger) Root Extract | 0.200 |
| Sodium Hyaluronate | 0.005 |
| Sodium Hyaluronate (Low Molecular Weight) | 0.005 |
| 90% Butylene Glycol (and) 5% Water (and) 4% Iris Florentina Root Extract solids (and) 1% Phenoxyethanol | 2.000 |
| Liposome w/Ceramide 3 & Sitosterol | 0.500 |
| Liposome w/Five Natural Oils & Tetrahexyldecyl ascorbate | 0.500 |
| Erythrulose (and) Water | 1.500 |
| Fragrance RTA-003511 Sheer Glow M1 | 0.200 |
| TOTAL | 100.000 |
| pH = | 3.5-4.0 |
| Viscosity = | 30,000-50,000 cP |
| LVT Spindle #4 @ 5 rpm for 60 seconds | |
| Specific Gravity = | 0.990-1.023 |

Formulation Example 12: Smooth Self-Tanning Cream. A personal care product composition in the form of a Smooth Self-Tanning Cream for skin darkening is prepared using the components and parameters shown Table 15 below.

TABLE 15

| Components of Formulation Example 12: Smooth Self-Tanning Cream | |
|---|---|
| Raw Material Description | % |
| Hydroxyethyl Acrylate/Sodium Acryloyldimethyl Taurate Copolymer (and) Polyisobutene (and) PEG-7 Trimethylolpropane Coconut Ether | 2.000 |
| Hydroxyethyl Acrylate/Sodium Acryloyldimethyl Taurate Copolymer (and) Isohexadecane (and) Polysorbate 60 | 1.000 |
| C12-15 Alkylbenzoate | 5.000 |
| Isodecyl Neopentanoate | 5.000 |
| Dimethicone, 5 cst | 5.000 |
| Hydrolyzed Jojoba Esters (and) Water | 1.000 |
| Water, Purified | 60.140 |
| Synthetic Fluorphlogopite (and) Titanium Dioxide (and) Iron Oxides (and) Tin Oxide | 1.000 |
| Synthetic Fluorphlogopite | 2.000 |
| Disodium EDTA | 0.100 |
| Dipotassium Glychrrhizinate | 0.050 |
| Dipropylene Glycol | 2.000 |
| Glycerin | 3.000 |
| Phenoxyethanol (and) Ethylhexylglycerin | 1.000 |
| Tocopheryl Acetate | 0.500 |

TABLE 15-continued

| Components of Formulation Example 12: Smooth Self-Tanning Cream | |
|---|---|
| Raw Material Description | % |
| Sodium Hyaluronate | 0.005 |
| Sodium Hyaluronate (Low Molecular Weight) | 0.005 |
| 90% Butylene Glycol (and) 5% Water (and) 4% Iris Florentina Root Extract solids (and) 1% Phenoxyethanol | 2.000 |
| Liposome w/Ceramide 3 & Sitosterol | 0.500 |
| Liposome w/Five Natural Oils & Tetrahexyldecyl ascorbate | 0.500 |
| Vitex Agnus Castus Extract & Acetyl Tyrosin & Glycerin & Alcohol & Water | 5.000 |
| Erythrulose (and) Water | 3.000 |
| Fragrance RTA-003511 Sheer Glow M1 | 0.200 |
| TOTAL | 100.000 |
| pH = | 3.5-4.0 |
| Viscosity = | TBD |

Formulation Example 13: Soothing After Sun Butter. A personal care product composition in the form of a Soothing After Sun Butter for skin darkening is prepared using the components and parameters shown Table 16 below.

TABLE 16

| Components of Formulation Example 13: Soothing After Sun Butter | |
|---|---|
| Raw Material Description | % |
| Water, Purified | 47.100 |
| Sodium Phytate (and) Water (and) Alcohol | 0.200 |
| Disodium EDTA | 0.100 |
| Dipotassium Glycyrrhizate | 0.030 |
| Glycerin | 5.000 |
| Tocopheryl Acetate | 0.200 |
| Water (and) CI 14700 | 0.720 |
| Water (and) CI 19140 | 1.740 |
| Lysolecithin (and) Sclerotium Gum (and) Xanthan Gum (and) Pullulan | 2.500 |
| Coco-Caprylate | 2.000 |
| Butyrospermum Parkii (Shea) Butter | 17.000 |
| Gossypium Herbaceum (Cotton) Seed Oil | 2.000 |
| Behenyl Alcohol | 1.500 |
| Glycerin (and) Water (and) Sodium Levulinate (and) Sodium Anisate | 4.000 |
| Glycerin (and) Water (and) Dextran (and) Acetyl Hexapeptide-1 | 0.500 |
| Dimethyl Isosorbide | 2.000 |
| Hydrolyzed Jojoba Esters (and) Water | 1.000 |
| Phenoxyethanol (and) Ethylhexylglycerin | 1.000 |
| Bisabolol (and) Zingiber Officinale (Ginger) Root Extract | 0.200 |
| Sodium Hyaluronate | 0.005 |
| Sodium Hyaluronate (Low Molecular Weight) | 0.005 |
| 90% Butylene Glycol (and) 5% Water (and) 4% Iris Florentina Root Extract solids (and) 1% Phenoxyethanol | 2.000 |
| Liposome w/Ceramide 3 & Sitosterol | 0.500 |
| Liposome w/Five Natural Oils & Tetrahexyldecyl ascorbate | 0.500 |
| Vitex Agnus Castus Extract & Acetyl Tyrosin & Glycerin & Alcohol & Water | 5.000 |
| Erythrulose (and) Water | 3.000 |
| Fragrance RTA-003511 Sheer Glow M1 | 0.200 |
| Citric Acid (25% Solution) | q.s. |
| TOTAL | 100.000 |
| pH = | 4.5-5.0 |
| Viscosity = | 30,000-60,000 CP |
| LVT Spindle #4 @ 6 rpm for 60 seconds | |

Formulation Example 14: Age Spot Serum. An Age Spot Serum was prepared using the components and paramters shown in Table 17 below. In a first phase, Part A, Purified Water was added to a container. Acrylates/C10-30 Alkyl Acrylate Crosspolymer was then sprinkled on the surface of the Water. The Acrylates/C10-30 Alkyl Acrylate Crosspolymer powder was then wet out and allowed to settle to the bottom of the container to form a Part A Mixture. The Part A Mixture was then mechanically agitated. The Part A Mixture was heated to 75-80° C. and Butylene Glycol, Hydroxyethylcellulose, Xanthan Gum, Disodium EDTA, Dipotassium Glycyrrhizate, Glycerin (and) Glyceryl Acrylate/Acrylic Acid Copolymer (and) PVM/MA Copolymer, Hydrogenated Lecithin, Chlorphenesin, Caprylyl Glycol, and Niacinamide were added to the Part A Mixture.

In a second phase, Part B, Diemthicone 1.5 cst was added to a container to form a Part B Mixture. The Part B Mixture was heated to 75-80° C. and Dimethicone 5 cst, Phenoxyethanol, Tocopheryl Acetate, dl-alpha-Tocopherol, Polymethylsilsesquioxane, Behenyl Alcohol (and) Polyglyceryl-10 Pentastearate (and) Sodium Stearoyl Lactylate, and Batyl Alcohol were added to the Part B Mixture.

In a third phase, the Part B Mixture was added to the Part A Mixture with homogenization on a Silverson Mill (3,700 rpm for 4 minutes) to form an Age Spot Serum Mixture. The Age Spot Serum Mixture was then mixed for 10 minutes at 75-80° C. The Age Spot Serum Mixture was then cooled to 32-50° C. At 50° C., Cytidine was added to the Age Spot Serum Mixture. At 40° C. and below, Liposome w/Ceramide & Beta-Sitosterol, Water (and) Acetyl Glucosamine (and) Xanthan Gum (and) *Chondrus crispus* (Carrageenan) (and) Glucose, Iris Florentina Root Extract, Hydrolyzed Opuntia *Ficus*-Indica Flower Extract, Fragrance UAK12854/00 Petals & Pearls Mod 4, and Potassium Hydroxide (45 wt. % Solution with water) were added to the Age Spot Serum Mixture. The Age Spot Serum Mixture was then mixed for 10 minutes and cooled to 32-35° C.

In a fourth phase, Purified Water is added to a container and mixed with Ascorbyl Glucoside, Sodium Citrate Dihyrdate, and Potassium Hydroxide (45 wt. % Solution with water) to form a Premix A Mixture. The Premix A Mixture was mixed until uniform, and was then added to the Age Spot Serum Mixture.

TABLE 17

| Components of Formulation Example 14 Age Spot Serum | | |
|---|---|---|
| Raw Material Description | Weight (%) | Weight (grams) |
| Water, Purified | 64.865 | 972.975 |
| Acrylates/C10-30 Alkyl Acrylate Crosspolymer [Carbopol Ultrez 20] | 0.200 | 3.000 |
| Butylene Glycol | 7.000 | 105.000 |
| Hydroxyethylcellulose | 0.170 | 2.550 |
| Xanthan Gum | 0.170 | 2.550 |
| Disodium EDTA | 0.150 | 2.250 |
| Dipotassium Glycyrrhizate | 0.030 | 0.450 |
| Glycerin( and) Glyceryl Acrylate/Acrylic Acid Copolymer (and) PVM/MA Copolymer [Lubragel Oil] | 0.250 | 3.750 |
| Hydrogenated Lecithin [Lecinol S10] | 1.000 | 15.000 |

TABLE 17-continued

Components of Formulation Example 14 Age Spot Serum

| Raw Material Description | Weight (%) | Weight (grams) |
|---|---|---|
| Chlorphenesin | 0.290 | 4.350 |
| Caprylyl Glycol | 0.700 | 10.500 |
| Niacinamide | 3.500 | 52.500 |
| Dimethicone 1.5 cst | 0.500 | 7.500 |
| Dimethicone 5 cst | 1.250 | 18.750 |
| Phenoxyethanol | 0.300 | 4.500 |
| Tocopheryl Acetate | 0.500 | 7.500 |
| dl-alpha-Tocopherol | 0.500 | 7.500 |
| Polymethylsilsesquioxane [Gransil PSQ] | 1.000 | 15.000 |
| Behenyl Alcohol (and) Polyglyceryl-10 Pentastearate (and) Sodium Stearoyl Lactylate [Nikkomulese 41] | 1.750 | 26.250 |
| Batyl Alcohol | 0.500 | 7.500 |
| Cytidine | 2.000 | 30.000 |
| Water, Purified | 4.000 | 60.000 |
| Ascorbyl Glucoside | 2.000 | 30.000 |
| Sodium Citrate Dihydrate | 0.200 | 3.000 |
| Potassium Hydroxide (45% Solution) | 0.725 | 10.875 |
| Liposome w/Ceramide & Beta-Sitosterol (Empty) | 1.000 | 15.000 |
| Water (and) Acetyl Glucosamine (and) Xanthan Gum (and) Chondrus Crispus (Carrageenan) (and) Glucose [NV Hexose PD Renewal-2X PF] | 1.000 | 15.000 |
| 91-92.3% Isononyl Isononanoate (and) 4.7-6% Water (and) 2% Iris Florentina Root Extract (and) 1% Phenoxyethanol | 2.000 | 30.000 |
| Hydrolyzed Opuntia Ficus-Indica Flower Extract [Exfoliactive SP] | 2.000 | 30.000 |
| Fragrance UAK12854/00 Petals & Pearls Mod 4 | 0.150 | 2.250 |
| Potassium Hydroxide (45% Solution) | 0.300 | 4.500 |
| TOTAL | 100.000 | 1500.000 |

Formulation Example 15: Age Spot Corrector. An Age Spot Corrector was prepared using the components and paramters shown in Table 18 below. In a first phase, Part A, Purified Water was added to a container. The water was then heated to 75-80° C. Glycerin, Ethoxydiglycol, Citric Acid, Sodium Citrate Dihydrate, Disodium EDTA, Dipotassium Glycyrrhizate, Hydrogenated Lecithin, Chlorphenesin, Sensiva SC50, Tranexamic Acid, and Potassium Hydroxide (45 wt. % Solution with water) were all added to the heated water to form a Part A Mixture. The pH was then adjusted to 6.8-7.2 for best active stability.

In a second phase, Part B, Caprylic/Capric Triglycerides, Squalane, Phenoxyethanol, Tocopheryl Acetate, and Polymethylsilsesquioxane were all added to a container to form a Part B mixture. The Part B mixture was then heated to 75-80° C. Arachidyl Alcohol (and) Behenyl Alcohol (and) Arachidyl Glucoside, Cetearyl Alcohol (and) Cetearyl Glucoside, and Sodium Acrylate/Acryloyldimethyltaurate Copolymer (and) Isohexadecane (and) Polysorbate 80 were then all added to the Part B mixture.

When both the Part A and Part B mixtures were at ~80° C., the Part B mixture was slowly added to the Part A mixture on a Silverston mill at 3,700 rpm for 4 minutes to form an Age Spot Corrector Mixture. The Age Spot Corrector Mixture was then returned to propeller mixing and cooled to 32-50° C.

In a third phase, Purified Water, Ascorbyl Glucoside, Sodium Citrate Dihydrate, and Potassium Hydroxide (45 wt. % Solution with water) were all mixed until uniform to form a Premix B Mixture. When the Age Spot Corrector Mixture was at a temperature of 50° C. the Premix B Mixture was added to the Age Spot Corrector Mixture. When the temperature of the Age Spot Corrector Mixture was at 40° C. and below Iris Florentina Root Extract, Fragrance UAK12854/00 Petals & Pearls Mod 4, and Potassium Hydroxide (45 wt. % Solution with water) were added to the Age Spot Corrector Mixture. The Age Spot Corrector Mixture was then mixed for 10 minutes and cooled to ~32-35° C. The final Age Spot Corrector was measured to have a pH of 6.5-7.5, a viscosity of ~150,000 cP.

TABLE 18

Components of Formulation Example 15 Age Spot Corrector

| Raw Material Description | Weight (%) | Weight (grams) |
|---|---|---|
| Water, Purified | 63.995 | 767.940 |
| Glycerin | 2.000 | 24.000 |
| Ethoxydiglycol | 1.000 | 12.000 |
| Citric Acid | 0.100 | 1.200 |
| Sodium Citrate Dihydrate | 0.900 | 10.800 |
| Disodium EDTA | 0.150 | 1.800 |
| Dipotassium Glycyrrhizate | 0.030 | 0.360 |
| Hydrogenated Lecithin [Lecinol S10] | 0.500 | 6.000 |
| Chlorphenesin | 0.290 | 3.480 |
| Sensiva SC50 | 1.000 | 12.000 |
| Tranexamic Acid | 1.000 | 12.000 |
| Potassium Hydroxide (45% Solution) | 0.300 | 3.600 |
| Caprylic/Capric Triglycerides | 5.000 | 60.000 |
| Squalane | 3.000 | 36.000 |
| Phenoxyethanol | 0.500 | 6.000 |
| Tocopheryl Acetate | 1.000 | 12.000 |
| Polymethylsilsesquioxane [Gransil PSQ] | 1.000 | 12.000 |
| Arachidyl Alcohol (and) Behenyl Alcohol (and) Arachidyl Glucoside [MONTANOV™ 202] | 3.000 | 36.000 |
| Cetearyl Alcohol (and) Cetearyl Glucoside [MONTANOV ™ 68] | 2.000 | 24.000 |
| Sodium Acrylate/Acryloyldimethyltaurate Copolymer (and) Isohexadecane (and) Polysorbate 80 [SIMULGEL ™ EG] | 4.000 | 48.000 |
| Water, Purified | 4.000 | 48.000 |
| Ascorbyl Glucoside | 2.000 | 24.000 |
| Sodium Citrate Dihydrate | 0.200 | 2.400 |
| Potassium Hydroxide (45% Solution) | 0.725 | 8.700 |
| 91-92.3% Isononyl Isononanoate (and) 4.7-6% Water (and) 2% Iris Florentina Root Extract (and) 1% Phenoxyethanol | 2.000 | 24.000 |
| Fragrance UAK12854/00 Petals & Pearls Mod 4 | 0.150 | 1.800 |
| Potassium Hydroxide (45% Solution) | 0.160 | 1.920 |
| TOTAL | 100.000 | 1200.000 |

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

The terms "comprising" or "comprise" are used herein in their broadest sense to mean and encompass the notions of "including," "include," "consist(ing) essentially of," and "consist(ing) of." The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-25, ±0-10, ±0-5, or ±0-2.5, % of the numerical values. Further, the term "about" applies to both numerical values when associated with a range of values. Moreover, the term "about" may apply to numerical values even when not explicitly stated.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

What is claimed is:

1. A method of preparing an Orris root extract, the method comprising:

extracting an Orris root material with a solvent system to give the Orris root extract, wherein the Orris root extract comprises germanaism B and is selectively enriched in (A) a phytochemical melanogenesis stimulating agent or (B) a phytochemical melanogenesis inhibiting agent;

wherein extracting comprises subjecting a dried Orris root feedstock to sequential first and second hydroethanolic solvent extractions, where the first hydroethanolic solvent extraction is performed using a 15:85 ($EtOH/H_2O$) hydroethanolic solvent system to give a first extract and an extracted feedstock, and where the second hydroethanolic solvent extraction is performed on the extracted feedstock using a 70:30 ($EtOH/H_2O$) hydroethanolic solvent system to give a second extract.

2. The method of claim 1, wherein the Orris root extract is enriched in the phytochemical melanogenesis stimulating agent (A), and wherein the phytochemical melanogenesis stimulating agent (A) is the germanaism B.

3. The method of claim 1, wherein the Orris root extract is enriched in the phytochemical melanogenesis inhibiting agent (B), and wherein the phytochemical melanogenesis inhibiting agent (B) comprises: (i) iriflorental; (ii) iripallidal; or (iii) both (i) and (ii).

4. The method of claim 1, wherein the Orris root material is further defined as rhizome of *Iris germanica* L., *Iris florentina* L., and/or *Iris pallida.*

5. The method of claim 1, wherein the dried Orris root feedstock comprises a moisture content of 5-15%.

6. The method of claim 1, wherein the first extract is enriched in germanaism B and depleted in iridals, iriflorental and iripallidal as compared to the Orris root material.

7. The method of claim 1, wherein the second extract is enriched in iridals, iriflorental and iripallidal and depleted in germanaism B as compared to the Orris root material.

* * * * *